(12) United States Patent
Fukui et al.

(10) Patent No.: US 8,552,355 B2
(45) Date of Patent: Oct. 8, 2013

(54) SMOKE SENSOR INCLUDING A CURRENT TO VOLTAGE CIRCUIT HAVING A LOW FREQUENCY CORRECTION MEANS TO PRODUCE A CORRECTION CURRENT

(75) Inventors: Suguru Fukui, Takatsuki (JP); Teruki Hatatani, Osaka (JP)

(73) Assignee: Panasonic Corporation, Kadoma-shi (JP)

( * ) Notice: Subject to any disclaimer, the term of this patent is extended or adjusted under 35 U.S.C. 154(b) by 409 days.

(21) Appl. No.: 12/736,598

(22) PCT Filed: Apr. 21, 2009

(86) PCT No.: PCT/JP2009/057922
§ 371 (c)(1),
(2), (4) Date: Oct. 21, 2010

(87) PCT Pub. No.: WO2009/131119
PCT Pub. Date: Oct. 29, 2009

(65) Prior Publication Data
US 2011/0031419 A1   Feb. 10, 2011

(30) Foreign Application Priority Data

Apr. 24, 2008  (JP) ................. 2008-114594
Nov. 20, 2008  (JP) ................. 2008-297161
Nov. 20, 2008  (JP) ................. 2008-297339
Dec. 19, 2008  (JP) ................. 2008-324558
Dec. 19, 2008  (JP) ................. 2008-324559

(51) Int. Cl.
*G01J 1/44* (2006.01)
*H03F 3/08* (2006.01)
*G01N 15/06* (2006.01)

(52) U.S. Cl.
USPC ............ 250/214 C; 250/214 R; 250/574

(58) Field of Classification Search
USPC ............ 250/221, 214 R, 214.1, 221.1, 214 A, 250/214 C, 573, 574, 575, 576, 222.2, 250/338.3, 338.1, 338.5, 339.06, 339.14, 250/339.15; 356/438, 436, 437, 439, 440, 356/441, 442, 433; 340/628, 540, 600, 603, 340/627, 630, 632; 327/514
See application file for complete search history.

(56) References Cited

U.S. PATENT DOCUMENTS 3,534,351 A    10/1970  Harnden, Jr. et al.
3,798,625 A *   3/1974  McMillian et al. ........... 340/527

(Continued)

FOREIGN PATENT DOCUMENTS

JP    03-030097 A    2/1991
JP    03-253999 A   11/1991

(Continued)

OTHER PUBLICATIONS

International Search Report dated Aug. 4, 2009, issued for PCT/JP2009/057922.

(Continued)

*Primary Examiner* — Pascal M Bui Pho
*Assistant Examiner* — Jennifer Bennett
(74) *Attorney, Agent, or Firm* — Edwards Wildman Palmer LLP

(57) ABSTRACT

A current-voltage converting circuit (2) is provided with a first feedback circuit (5) and a correcting transistor (Q1). The first feedback circuit (5) outputs, of an output voltage (V10), a voltage according to a magnitude of a low-frequency component that is not greater than or equal to a predefined first cut-off frequency. The correcting transistor (Q1) extracts a correction current (I21) according to a magnitude of an output of the first feedback circuit (5) from a sensor current (I10). The first feedback circuit (5) has a first integrating circuit (9) and a sample-and-hold circuit (10). The first integrating circuit (9) integrates the output voltage (V10) of a conversion section (3). The sample-and-hold circuit (10) samples and holds an output of the first integrating circuit (9) during a sensing period at which a pulsed detection signal is inputted. Means for preventing an incidence of ambient light onto a light-receiving section can be simplified or omitted as a result.

18 Claims, 21 Drawing Sheets

(56) References Cited

U.S. PATENT DOCUMENTS

| | | | |
|---|---|---|---|
| 4,225,791 A | | 9/1980 | Kompelien |
| 5,025,169 A | * | 6/1991 | Arakawa et al. ............. 250/574 |
| 5,477,218 A | | 12/1995 | Manmoto et al. |
| 5,497,009 A | | 3/1996 | Torikoshi et al. |
| 5,872,634 A | * | 2/1999 | Kunz ............................ 356/438 |
| 2009/0212867 A1 | * | 8/2009 | Fukuzawa et al. ............ 330/284 |

FOREIGN PATENT DOCUMENTS

| | | | |
|---|---|---|---|
| JP | 2783945 B2 | | 2/1994 |
| JP | 07-151680 A | | 6/1995 |
| JP | 07-175984 A | | 7/1995 |
| JP | 09-106488 A | | 4/1997 |
| JP | 10-154285 A | | 6/1998 |
| JP | 10281866 A | * | 10/1998 |

OTHER PUBLICATIONS

Supplementary European Search Report dated Jun. 24, 2013, issued for the European patent application No. 09736033.3.

\* cited by examiner (a) INPUT CURRENT (b) OUTPUT SIGNAL (THERE IS A FIRE)

(c) OUTPUT SIGNAL (THERE IS NO SMOKE)

(a) OUTPUT SIGNAL (b) INPUT CURRENT

TIME (a) INPUT CURRENT (b) OUTPUT SIGNAL

OPERATING POINT
AD0
AD1  AD2

DYNAMIC RANGE

TIME (a) POWER SOURCE (b) LED (c) OUTPUT

FIRE DETERMINATION LEVEL

ΔV

TIME

SMOKE SENSOR INCLUDING A CURRENT TO VOLTAGE CIRCUIT HAVING A LOW FREQUENCY CORRECTION MEANS TO PRODUCE A CORRECTION CURRENT

TECHNICAL FIELD

The invention relates to a smoke sensor that detects smoke generated during a fire and that sets off an alarm.

BACKGROUND ART

In known configurations, (for instance, Japanese Patent No. 2783945) such a conventional smoke sensor A comprises, for instance, a housing 20, an LED (light-emitting section) 6, and a photodiode (light-receiving section) PD, as illustrated in FIG. 30(a). In the smoke sensor A disclosed in Japanese Patent No. 2783945, the LED 6 outputs light intermittently towards a sensing space within the housing 20, while the photodiode PD, which is disposed at a position on which direct light from the LED 6 is not incident, converts the received light into current. When smoke flows into the sensing space of the smoke sensor A, the smoke gives rise to diffusion and reflection of light from the LED 6 within the sensing space. This causes an increase in the amount of light, from the LED 6, that is received by the photodiode PD, and thereby increases the amount of current outputted by the photodiode PD.

The LED 6 and the photodiode PD comprise a projection lens 23 disposed in front of the LED 6, a light-receiving lens 24 disposed in front of the photodiode PD, and an optical block 25. The housing 20 comprises a body 26 and a cover 27. The body 26 houses the optical block 25, which has an opening in its lower face, in such a manner that light from the LED 6 exits towards the opening. The cover 27 has a bottomed tubular shape, with an opening at its top face, and is joined to the body 26 so as to cover the opening of the body 26. An opening window for smoke intake is formed in the peripheral wall of the cover 27. The sensing space is formed inside the cover 27. An insect screen 28 that prevents the intrusion of insects into the sensing space, and a labyrinth 21 that prevents ambient light from being incident into the sensing space, are disposed inside the cover 27, so as to surround the sensing space. The labyrinth 21 uses a complex structure having convoluted optical paths in order to prevent intrusion of various types of ambient light, for instance from fluorescent lamps, incandescent lamps or the like, and to prevent the photodiode PD from being struck by light from the LED 6 in a state where no smoke is in the sensing space.

In such a smoke sensor A, a current-voltage conversion circuit (IV conversion circuit) 2 that converts an input current, from the photodiode PD, into voltage, and that outputs the voltage, is provided in a circuit block 1 housed in the housing 20, as illustrated in FIG. 30(b). The smoke sensor A is configured in such a manner that the output voltage from the current-voltage conversion circuit 2 passes through an amplifier circuit 12 and a filter circuit 13, is inputted to a alarm set-off determination circuit 14 that is a determination processing section, and an alarm is set off by the alarm set-off circuit 15 (buzzer or the like) when the amount of change of the output voltage exceeds a predefined fire determination level. The circuit block 1 comprises a power source circuit 16 that supplies power to the various circuits, a driving circuit 17 that drives, for instance, other alarm set-off means, and a LED driving circuit 18 that causes the LED 6 to periodically emit light in pulses. The LED driving circuit 18 comprises a transistor Tr1 (FIG. 31) connected in series with respect to the LED 6.

The current-voltage conversion circuit 2 used herein has a conversion section 3 that comprises an operational amplifier OP1, for instance as illustrated in FIG. 31. In the conversion section 3, a converting resistor R2 is connected between an inverting input terminal and an output terminal of the operational amplifier OP1. The conversion section 3 is configured in such a manner so as to output, at an output terminal Tout, an output voltage V10 whose value fluctuates according to fluctuation of an input current I20 that is inputted to the inverting input terminal. In the example of FIG. 31, a reference voltage Vs is applied to a non-inverting input terminal. Therefore, the output voltage V10 is represented by $V10 = Vs - (I20 \times r2)$, wherein r2 is the resistance value of the converting resistor R2. The current-voltage conversion circuit 2 causes the output voltage V10 to fluctuate with reference to an operating point, in accordance with the fluctuation of the input current I20, taking, as the operating point, the output voltage V10 at a steady state where the photodiode PD is not receiving light from the LED 6.

Thanks to their straightforward installation, recent years have witnessed a growing demand for smoke sensors A having batteries as a power source. When using a battery as a power source of a smoke sensor A, the latter must be driven intermittently in order to prolong the life of the battery and curb the average power consumption of the smoke sensor A. In this case, power is supplied intermittently to the current-voltage conversion circuit 2 illustrated in (a) of FIG. 32. Therefore, the LED 6 is driven so as to output pulsed light during the time at which power is supplied to the current-voltage conversion circuit 2, as illustrated in (b) of FIG. 32. When the photodiode PD receives light from the LED 6, upon intrusion of smoke into the sensing space, the amount of change $\Delta V$ of the output voltage V10 of the current-voltage conversion circuit 2 becomes greater, and reaches a fire determination level in the figure, as indicated by the solid line of (c) of FIG. 32. If, by contrast, no smoke is present in the sensing space, the amount of change $\Delta V$ of the output voltage is small and does not reach the fire determination level, as indicated by the broken line in (c) of FIG. 32.

In a current-voltage conversion circuit 2 such as the one in FIG. 31, a dynamic range of the operational amplifier OP1 is restricted between a power source voltage VDD and a ground GND of the operational amplifier OP1, as illustrated in FIG. 33(a). The above-described output voltage V10 fluctuates as a result within the dynamic range. Therefore, the output voltage V10 becomes saturated when the input current I20 is equal to or greater than a given magnitude.

For instance, the sensing space in the above-described smoke sensor A cannot be completely cut off from the exterior, even despite the presence of the labyrinth 21, and hence ambient light, though little, strikes the photodiode PD. Ordinarily, the ambient light exhibits little fluctuation over time. Thus, when receiving the ambient light, the photodiode PD outputs a current having little fluctuation over time (hereafter, low-frequency component). The output voltage V10 may become saturated in some cases when the low-frequency component comprised in the input current I20 is equal to or greater than a certain magnitude.

Specifically, the operating point of the output voltage V10 becomes the reference voltage Vs, as illustrated in FIG. 33(a), if the input current I20 comprises no low-frequency component. If the input current I20 fluctuates, therefore, the output voltage V10 also fluctuates following the fluctuation of the input current I20. By contrast, the operating point of the output voltage V10 drops, as illustrated in FIG. 33(b), when the input current I20 comprises a low-frequency component. If the input current I20 increases, the output voltage V10 may become saturated halfway through. In particular, the output voltage V10 is brought to a saturated state, regardless of the fluctuation of the input current I20, and the output voltage V10 fails to follow the increase in the input current I20, if the low-frequency component is large and the operating point of the output voltage V10 is lowered down to about ground GND, as illustrated in FIG. 33(c).

For instance, the voltage drop between the terminals of the converting resistor R2 is 1 V for an input current I20 of 1 µA, assuming a resistance value r2 of 1 MΩ for the converting resistor R2, and a reference voltage Vs of 1 V. As a result, the output voltage V10 of the current-voltage conversion circuit 2 becomes saturated, at 0 V. In this state, the output voltage V10 of the current-voltage conversion circuit 2 is saturated, and hence does not fluctuate any further, even if the pulsed input current I20 is inputted to the current-voltage conversion circuit 2 upon reception, by the photodiode PD, of light from the LED 6. In this case, therefore, there is a chance of alarm failure in that the amount of change ΔV of the output voltage V10 does not reach a fire determination level.

Such a smoke sensor A, moreover, may conceivably be configured so as to set off an alarm when an instantaneous value of the output voltage V10 reaches a predefined fire determination level. In this case as well, there is a chance of alarm failure and false alarms when the operating point itself of the output voltage V10 fluctuates due to the influence of the low-frequency component, even if the output voltage V10 is not saturated. An alarm failure occurs when the output voltage V10 does not reach the fire determination level, despite the presence of smoke in the sensing space, and a false alarm occurs when the output voltage V10 reaches the fire determination level, despite the absence of smoke in the sensing space.

In the above smoke sensor A, the labyrinth 27 prevents ambient light from striking into the sensing space, and hence suppresses fluctuation of the operating point of the output voltage V10 due to the influence of ambient light, so that the above-described alarm failures and false alarms are unlikely to occur.

In the above-described smoke sensor A, however, the labyrinth 21 that prevents ambient light from being incident into the sensing space has a complex structure. The manufacturing cost of the labyrinth 21 precludes reducing the costs of the smoke sensor A as a whole. It would therefore be desirable to lower the cost of the smoke sensor A as a whole by simplifying the structure of the labyrinth 21 as much as possible, or by omitting the labyrinth 21 itself.

However, simplifying or omitting the labyrinth 21 results in a greater ambient light intensity being received by the photodiode PD, and in a greater low-frequency component comprised in the input current I20, which causes the operating point of the output voltage V10 to fluctuate. Alarm failures and false alarms become likelier as a result, which is problematic. In the particular case where the smoke sensor A uses a battery as a power source, as described above, the power source voltage of the operational amplifier OP1 is low, and the dynamic range of the operational amplifier OP1 is comparatively narrow. As a result, the output voltage V10 saturates readily.

DISCLOSURE OF THE INVENTION

It is an object of the present invention to provide a smoke sensor in which means for preventing the incidence of ambient light onto a light-receiving section can be simplified or omitted.

A smoke sensor according to the present invention includes: a light-emitting section; a light-receiving section; a current-voltage conversion circuit; a current source; and a determination processing section. The light-emitting section outputs pulsed light towards a sensing space at a predefined sensing period. The light-receiving section is disposed at a position not struck by direct light from the light-emitting section, but struck by light from the light-emitting section, that is diffused and reflected by smoke that flows into the sensing space. The current source is configured so as to cause a sensor current of a magnitude corresponding to a light reception intensity to flow in the light-receiving section. The current-voltage conversion circuit has a conversion section, and the conversion section is configured so as to convert an input current to an output voltage, and to output the output voltage from an output terminal. The input current is inputted to an input terminal of the conversion section connected to the light-receiving section. The determination processing section is configured so as to determine presence or absence of the smoke in the sensing space on a basis of the output voltage. The current-voltage conversion circuit has a low-frequency correction means. The low-frequency correction means extracts, of the output voltage, a low-frequency component that is not greater than or equal to a cut-off frequency that is lower than a frequency of a pulsed detection signal that is generated when the light-receiving section receives light from the light-emitting section, causes a flow of a correction current of a magnitude according to the low-frequency component, and uses a combined current of the correction current and the input current as the sensor current, to reduce thereby the input current by the correction current.

In the above configuration, if the current flowing through the light-receiving section comprises a low-frequency component, the low-frequency correction means can suppress, saturation of the output voltage due to the low-frequency component, through feedback between an output terminal and an input terminal. That is, the low-frequency correction means causes the flow of a correction current of a magnitude according to the low-frequency component, whereby the low-frequency component is subtracted from the input current, and there is suppressed the influence of the low-frequency component on the output voltage. Therefore, it is possible to suppress the influence of the low-frequency component on the output voltage that is generated at the output terminal of the conversion section, even when the low-frequency component comprised in the sensor current that flows through the light-receiving section is comparatively large on account of strong ambient light being received by the light-receiving section. As a result, means for preventing the incidence of ambient light onto the light-receiving section can be simplified or omitted.

In a more preferred embodiment, the sensor current is a current flowing from the light-receiving section into the input terminal, and the low-frequency correction means is configured so as to extract, from the light-receiving section, a current of a magnitude corresponding to the correction current.

In the above configuration, the low-frequency correction means extracts the correction current from the light-receiving section. Thereby, the low-frequency component is subtracted from the input current that is inputted to the conversion section, and there can be suppressed the influence of the low-frequency component on the output voltage.

In another preferred embodiment, the sensor current is a current flowing from the conversion section into the light-receiving section, and the low-frequency correction means is configured so as to supply, to the light-receiving section, a current of a magnitude corresponding to the correction current.

In the above configuration, the low-frequency correction means supplies the correction current to the light-receiving section, whereby the low-frequency component is subtracted from the input current that is supplied from the conversion section to the light-receiving section, and there can be suppressed the influence of the low-frequency component on the output voltage.

In a yet more preferred embodiment, the low-frequency correction means comprises a first feedback circuit and a correcting transistor. The first feedback circuit outputs, of the output voltage, a low-frequency component that is not greater than or equal to a first cut-off frequency that is lower than a frequency of the detection signal. The correcting transistor is inserted between a predefined potential point and the input terminal, and is configured in such a manner that a control terminal is connected to an output of the first feedback circuit, whereby the correction current of a magnitude according to the output of the first feedback circuit is caused to flow.

In the above configuration, a low-frequency component no greater than the first cut-off frequency can flow, as a correction current, in the correcting transistor, and hence there can flow a correction current that is larger than in a case where the correction current flows through a resistor. Therefore, it is possible to suppress the influence of the low-frequency component on the output voltage that is generated at the output terminal of the conversion section, even when the low-frequency component comprised in the input current is comparatively large on account of strong ambient light being received by the light-receiving section. As a result, means for preventing the incidence of ambient light onto the light-receiving section can be simplified or omitted.

In another preferred embodiment, the low-frequency correction means comprises a second feedback circuit and a correcting resistor. The second feedback circuit outputs, of the output voltage, a voltage corresponding to a low-frequency component that is not greater than or equal to a second cut-off frequency that is lower than a frequency of the detection signal. The correcting resistor is inserted between an output of the second feedback circuit and the input terminal, and is configured in such a manner to cause a flow of the correction current of a magnitude according to the output of the second feedback circuit.

In the above configuration, a low-frequency component no greater than the second cut-off frequency can flow, as a correction current, to the correcting resistor. Hence, there can be widened the upper limit for the magnitude of the low-frequency component whose influence on the output voltage can be suppressed, as compared with a case in which the correction current flows only in the correcting transistor. Accordingly, there can be suppressed the influence of the low-frequency component on the output voltage that is generated at the output terminal of the conversion section, as compared with a case in which the input current comprises a larger low-frequency component.

In yet another preferred embodiment, the first feedback circuit has frequency switching means. The frequency switching means is configured so as to switch the first cut-off frequency to be lower than the second cut-off frequency at the sensing period, and be higher than the second cut-off frequency at a period other than the sensing period.

In the above configuration, the first feedback circuit allows avoiding the flow of the detection signal in the correcting transistor, in the sensing period, even if a comparatively wide low-frequency component flows to the correcting transistor at periods other than the sensing period. In the sensing period, the second feedback circuit allows the low-frequency component no greater than the second cut-off frequency to flow in the correcting resistor.

In yet another preferred embodiment, the first feedback circuit has an integrating circuit that outputs an integration value component of the output voltage. The frequency switching means comprises a sample-and-hold-circuit, and the sample-and-hold-circuit has a first switch inserted between an output of the integrating circuit and the control terminal of the correcting transistor. At the sensing period, the frequency switching means is configured so as to switch off the first switch, to operate thereby the sample-and-hold-circuit, and so as to apply a held output voltage of the integrating circuit to the control terminal of the correcting transistor.

In the above configuration, the output of the integrating circuit is cut off from the control terminal of the correcting transistor through switching-off of the first switch, in the sensing period. As a result, there can be prevented the influence that is exerted, on input, by stationary noise, such as flicker noise or the like, generated at the integrating circuit. The SN ratio is thus increased.

In yet another preferred embodiment, a second switch is connected between the output terminal and the input terminal of the conversion section. The second switch is switched on when the first switch is on.

In the above configuration, the gain between the output terminal and the input terminal of the conversion section is lowered through switching-on of the second switch. System oscillation caused by switching-on of the first switch can be suppressed thereby.

In yet another preferred embodiment, an off resistance value of the first switch is set to be smaller than a resistance value between the predefined potential point and the control terminal of the correcting transistor.

Such a configuration allows a small current to flow through the off-resistance of the first switch, even at the sensing period at which the first switch is switched off. Thereby, the potential of the control terminal of the correcting transistor can be prevented from dropping due to leakage current that occurs between the control terminal of the correcting transistor and a predefined potential point. There can be suppressed, as a result, fluctuation of the output voltage caused by a drop in the potential of the control terminal of the correcting transistor.

In yet another preferred embodiment, the first feedback circuit has an integrating circuit that outputs an integration value component of the output voltage. The frequency switching means comprises a low-pass filter circuit, and the low-pass filter circuit has a parallel circuit of a capacitor, a resistor and a third switch. The capacitor is connected between the predefined potential point and the control terminal of the correcting transistor, and the parallel circuit is connected between the control terminal of the correcting transistor and an output of the integrating circuit. At the sensing period, the frequency switching means is configured so as to switch off the third switch, to operate thereby the low-pass filter circuit.

In such a configuration, current can flow through the resistor also during the sensing period, at which time the third switch is switched off. Thereby, the potential of the control terminal of the correcting transistor can be prevented from dropping due to leakage current that occurs between the control terminal of the correcting transistor and a predefined potential point. There can be suppressed, as a result, fluctuation of the output voltage caused by a drop in the potential of the control terminal of the correcting transistor. Also, the first cut-off frequency can be set, with good precision, in the sensing period. Therefore, the first cut-off frequency can be set higher, within a range such that the detection signal does not flow in the correcting transistor. A comparatively wide low-frequency component can flow as a result to the correcting transistor, also during the sensing period.

In yet another preferred embodiment, the first feedback circuit has an integrating circuit, and the integrating circuit has a time constant determined by a first resistor and a capacitor. The frequency switching means comprises a series circuit of a second resistor and a fourth switch, and the series circuit is connected in parallel to the first resistor. At the sensing period, the frequency switching means is configured so as to switch off the fourth switch.

This configuration allows reducing circuit size and power consumption as compared with a case in which a sample-and-hold-circuit is provided. Also, the first cut-off frequency can be set, with good precision, in the sensing period. Therefore, the first cut-off frequency can be set higher, within a range such that the detection signal does not flow into the correcting transistor. A comparatively wide low-frequency component can flow as a result in the correcting transistor, also during the sensing period.

In yet another preferred embodiment, the second feedback circuit comprises a second active filter, and the second active filter outputs a voltage of opposite phase to the input current. The first feedback circuit comprises a first active filter, and the first active filter is configured so as to output a voltage in-phase with the input current.

In such a configuration, an active filter is realized by the first and second feedback circuits. Hence, the first and second feedback circuits can have high gain towards the low-frequency component, and there can be reliably suppressed fluctuation of the output voltage due to the low-frequency component.

In yet another preferred embodiment, the second feedback circuit comprises a second active filter, and the second active filter outputs a voltage in-phase with a current that is supplied from the conversion section to the light-receiving section. The first feedback circuit comprises a first active filter, and the first active filter is configured so as to output a voltage of opposite phase to a current that is supplied from the conversion section to the light-receiving section.

In such a configuration, an active filter is realized by the first and second feedback circuits. Hence, the first and second feedback circuits can have high gain towards the low-frequency component, and there can be reliably suppressed fluctuation of the output voltage due to the low-frequency component.

In a more preferred embodiment, the correcting transistor is provided in a plurality, and the current-voltage conversion circuit comprises selection switches and a switch control circuit. The selection switches are inserted between the input terminal and the respective correcting transistors. The switch control circuit controls switching-on and -off of the selection switches in accordance with the output of the first feedback circuit in such a manner that the number of the selection switches that are switched on is greater as the output of the first feedback circuit is greater.

In the above configuration, the larger the correction current is, the greater becomes the number of correcting transistor through which the correction current flows. This allows keeping small the ratio between channel width and channel length in the respective correcting transistors, while allowing for significant correction of the input current. Stationary noise per correcting transistor can be kept small as a result.

In a more preferred embodiment, the first feedback circuit and the second feedback circuit share an operational amplifier, and the current-voltage conversion circuit comprises mode switching means. The mode switching means is configured so as to switch between an operation mode of using the operational amplifier in the first feedback circuit, and an operation mode of using the operational amplifier in the second feedback circuit.

In the above configuration, the first feedback circuit and the second feedback circuit share an operational amplifier, and hence the circuit can be made smaller than in a state where an operational amplifier is provided in each feedback circuit.

In a more preferred embodiment, a power source voltage of the first feedback circuit is set to be higher than the power source voltage of other Circuits.

In the above configuration, the upper limit value of the output of the first feedback circuit is higher than in a case where the power source voltage of the first feedback circuit is identical to the power source voltage of other circuits. This allows widening the upper limit of the magnitude of the current that can flow in the correcting transistor.

In another preferred embodiment, a smoke sensor according to the present invention includes: a light-emitting section; a light-receiving section; a sensor output processing section; and an operation processing section. The light-emitting section outputs pulsed light intermittently towards a sensing space. The light-receiving section is disposed at a position not struck by direct light from the light-emitting section, but struck by light from the light-emitting section, that is diffused and reflected by smoke that flows into the sensing space, and is configured in such a manner that the light-receiving section receives light and converts the light into a current. The sensor output processing section converts an input current, inputted by the light-receiving section, into an output voltage. The operation processing section is configured so as to determine presence or absence of the smoke in the sensing space on a basis of the output voltage. When the input current fluctuates, the sensor output processing section transiently changes an instantaneous value of the output voltage in accordance with the fluctuation amount. The operation processing section has detection means and determination means. The detection means detects, as respective measurement values, an instantaneous value of the output voltage at a first sampling timing and a second sampling timing set to be a transient response period of the output voltage for the input current. The determination means detects the presence or absence of the smoke in the sensing space by comparing a predefined threshold value with a difference value between the two measurement values detected by the detection means. The first sampling timing and second sampling timing are set so as to elicit a difference between the two measurement values.

In the above configuration, the operation processing section detects, as respective measurement values, an instantaneous value of the output voltage at a first sampling timing and a second sampling timing that are set to a transient response period of the output voltage for the input current. The operation processing section determines the presence or absence of smoke in the sensing space by comparing a predefined threshold value with a difference value between the two measurement values. Hence, the low-frequency component exerts virtually no influence on the difference value, even upon fluctuation of the operating point of the output voltage due to a large low-frequency component comprised in the input current. Therefore, the presence or absence of smoke in the sensing space can be determined while free of the influence of the low-frequency component. As a result, the labyrinth can be simplified or omitted, while avoiding alarm failures and false alarms, which is advantageous.

In a more preferred embodiment, the sensor output processing section has band pass means, and the band pass means is configured so as to generate a gain peak at a frequency band decided in accordance with a pulse width of light from the light-emitting section. The sensor output processing section outputs the output voltage as a signal that oscillates between both positive and negative sides of an operating point that is an instantaneous value in a state where the light-receiving section is not receiving light from the light-emitting section. The detection means detects the measurement values on both sides of the operating point, respectively.

In such a configuration, the detection means detects measurement values on both sides of the operating point of the output voltage. Therefore, the difference value between both measurement values can be greater than in a state where both measurement values are detected on one side of the operating point. The SN ratio increases thereby, which is advantageous.

In a more preferred embodiment, the band pass means has an integrating circuit and a differentiating circuit, and the integrating circuit is configured so as to integrate the input current, and the differentiating circuit is configured so as to differentiate an output of the integrating circuit.

In such a configuration, the output voltage can thus be made into a signal that oscillates between the positive and negative side of the operating point of the output voltage, by way of a comparatively simple configuration that utilizes an integrating circuit and a differentiating circuit.

In another preferred embodiment, a pulse width of light from the light-emitting section and the first sampling timing and second sampling timing are decided on a basis of a same clock.

Even if the pulse width of light from the light-emitting section varies due to, for instance, the temperature characteristic of the driving circuit of the light-emitting section, the above configuration allows the first sampling timing and second sampling timing to vary in response to the variability of the pulse width. As a result there can be suppressed the variability in the measurement values that arises on account of the variability of the pulse width of light from the light-emitting section.

In yet another preferred embodiment, the first sampling timing and second sampling timing are set to be ahead of an instantaneous value peak of the output voltage.

Even if the gain of the sensor output processing section varies due to, for instance, the temperature characteristic of the sensor output processing section, the above configuration allows keeping small the variability of the measurement values, arising from the above-mentioned gain variability, as compared with a case in which the measurement values are detected at a peak of the instantaneous value of the output voltage.

In yet another preferred embodiment, the operation processing section is configured so as to read, as a preliminary value, an instantaneous value of the output voltage at a preliminary period before output of light by the light-emitting section, and determination by the determination means is not carried out if the preliminary value is not within a normal range decided beforehand.

In the above configuration, determination by the determination means is not carried out in a state where the operating point itself of the output voltage fluctuates and deviates from a normal range due to the influence of the low-frequency component. This allows preventing alarm failures that occur through saturation of the output voltage, due to the influence of the low-frequency component, and through failure of detecting accurately the fluctuation amount of output voltage that derives from reception, by the light-receiving section, of light from the light-emitting section.

In yet another preferred embodiment, the sensor output processing is driven intermittently, and the light-emitting section is configured so as to output light during the driving of the sensor output processing section.

This configuration allows keeping average power consumption lower than in a case where the sensor output processing section is driven at all times. The presence or absence of smoke in the sensing space can still be determined, while free of the influence of fluctuation of the output voltage during startup of the sensor output processing section, even if the instantaneous value of the output voltage fluctuates during startup of the sensor output processing section.

In yet another preferred embodiment, the detection means comprises an AD converter, and the AD converter is configured so as to quantize the instantaneous value to obtain thereby the measurement value comprising a digital value.

In the above configuration, the detection means comprises an AD converter, and hence the circuit configuration of the operation processing section can be comparatively simple.

In another preferred embodiment, a smoke sensor according to the present invention includes: a light-emitting section; a light-receiving section; a detection processing section; and a determination processing section. The light-emitting section intermittently outputs light into a sensing space. The light-receiving section is disposed at a position not struck by direct light from the light-emitting section, but struck by light from the light-emitting section, that is diffused and reflected by smoke that flows into the sensing space. The detection processing section is configured so as to obtain a detection value corresponding to a smoke concentration in the sensing space on a basis of light reception intensity at the light-receiving section. The determination processing section is configured so as to determine presence or absence of fire on a basis of the detection value. Further, the determination processing section has storage means and determination means, the storage means stores a plurality of determination levels, and the determination means compares the detection value with the determination levels. The determination levels include a reference level, a fire determination level and a state determination level. The reference level corresponds to the detection value in a state where no smoke is in the sensing space. The fire determination level is set higher than the reference level and constitutes a criterion for fire, and the state determination level is set lower than the fire determination level and is calculated using at least one from among the reference level and the fire determination level. The determination means is configured so as to determine that there is a fire if the detection value is equal to or greater than the fire determination level, and to determine a predefined operating state in accordance with a magnitude relationship between the detection value and the state determination level, if the detection value is smaller than the fire determination level.

In the above configuration, the determination means determines that there is a fire if the detection value is equal to or greater than the fire determination level, and determines a predefined operating state in accordance with a magnitude relationship between the detection value and the state determination level, if the detection value is smaller than the fire determination level. Hence, both the operating state and the presence or absence of fire can be determined in a single process of comparing the detection value and the determination level. This is advantageous in that greater complexity of the circuit configuration is avoided, and longer times required for determinations are likewise avoided, even under concurrent determination of an operating state other than the presence or absence of fire, as compared with a case in which only fire determination is carried out.

In a more preferred embodiment, the state determination level includes a malfunction determination level set lower than the reference level, and the determination means is configured so as to determine the operating state to be a malfunction if the detection value is smaller than the malfunction determination level.

In the above configuration, a malfunction can be determined to have occurred when the detection value lies outside a normal range, due to, for instance, abnormalities in an optical system.

In a yet more preferred embodiment, the malfunction determination level is calculated using the reference level.

In this configuration, the malfunction determination level need not be set independently, and thus the setting of the determination level can be made less burdensome, which is advantageous.

In yet another preferred embodiment, the state determination level includes a contamination determination level set higher than the reference level. The determination means is configured so as to determine the operating state to be presence of contamination in the sensing space, if the detection value is equal to or greater than the contamination determination level and smaller than the fire determination level, and to correct the fire determination level in the storage means to a higher level, if contamination is determined to be present with a frequency equal to or greater than a prescribed value, upon confirmation of presence or absence of contamination at a predefined timing.

In the above configuration, the fire determination level in the storage means is corrected to a higher level if contamination is determined to be present with a frequency equal to or greater than a prescribed value, upon confirmation of presence or absence of contamination at a predefined timing. Therefore, the frequency of correction can be reduced vis-à-vis conventional configurations in which subtractive correction is required every time that fire determination is carried out. This is advantageous in that, as a result, it becomes possible to reduce the number of processes required for determining the occurrence of fire, vis-à-vis conventional cases, while preventing the occurrence of false alarms due to contamination in the sensing space.

In a more preferred embodiment, the contamination determination level is calculated using both the reference level and the fire determination level.

In this configuration, the contamination determination level need not be set independently, and thus the setting of the determination level can be made less burdensome, which is advantageous. Moreover, the contamination determination level is calculated using the fire determination level, and hence the contamination determination level as well is corrected when the fire determination level is corrected. This makes it unnecessary to correct the contamination determination level when the sensing space is contaminated.

BRIEF DESCRIPTION OF THE DRAWINGS

FIGS. 26(a) and 26(b) illustrate the configuration of Embodiment 9 of the present invention, wherein FIG. 26(a) is a schematic plan-view diagram, and FIG. 26(b) is a schematic partial longitudinal cross-sectional diagram;

FIGS. 28(a) and 28(b) illustrate another configuration of Embodiment 9, wherein FIG. 28(a) is a schematic plan-view diagram, and FIG. 28(b) is a schematic partial longitudinal cross-sectional diagram;

FIGS. 30(a) and 30(b) illustrate a conventional smoke sensor, wherein FIG. 30(a) is a schematic diagram and FIG. 30(b) a circuit block diagram;

BEST MODE FOR CARRYING OUT THE INVENTION

Embodiment 1

A smoke sensor A of the present embodiment has a sensing space in a housing 20. Further, the smoke sensor A has a light-emitting section, a light-receiving section and a circuit block 1. The light-emitting section intermittently outputs pulsed light towards the sensing space. The light-receiving section is disposed at a position at which direct light from the light-emitting section is not incident, and converts received light into current. The circuit block 1 is configured in such a manner so as to detect smoke in the sensing space, on the basis of an input current from the light-receiving section. When smoke flows into the sensing space in the smoke sensor A, the light from the light-emitting section is diffused and reflected by the smoke in the sensing space, as a result of which there increases the amount of light from the light-emitting section received at the light-receiving section, and there increases the amount of current outputted by the light-receiving section. In the smoke sensor A exemplified herein, a battery is used as a power source. Driving is performed intermittently in order to curb average power consumption and to prolong battery life.

Figure 30A:
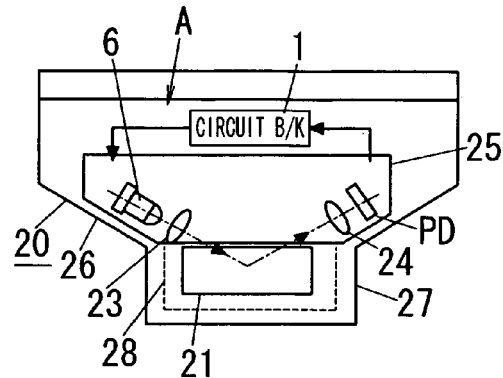
Figure 30B:
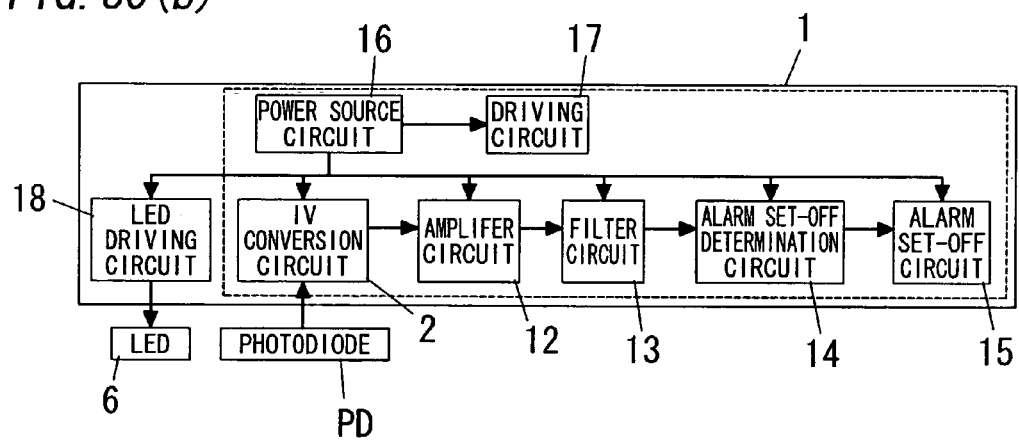
Figure 31:
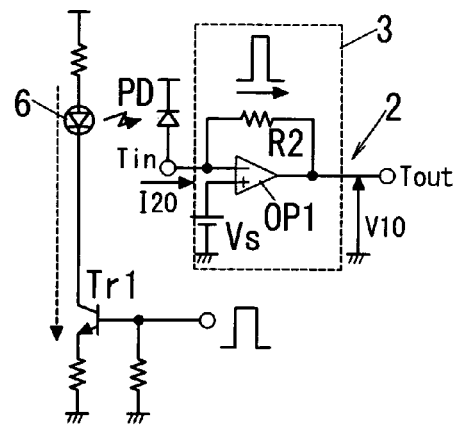
FIG. 31 is a schematic circuit diagram illustrating a current-voltage conversion circuit of the conventional smoke sensor.
Figure 32:
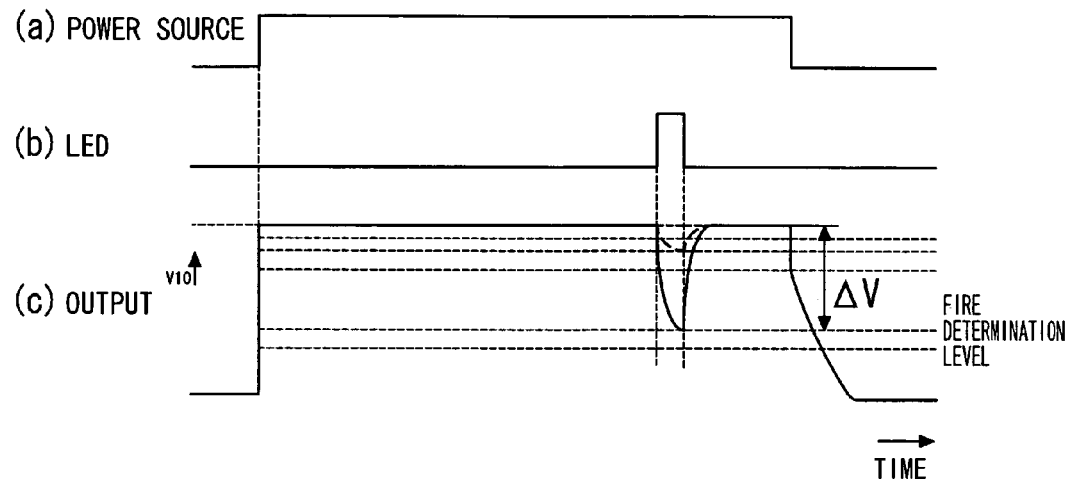
FIG. 32 is a timing chart illustrating the operation of the conventional smoke sensor.
Figure 33:
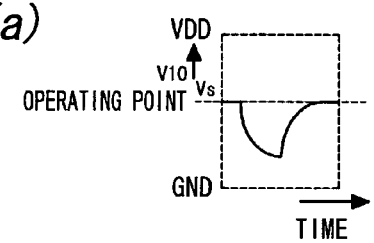
FIGS. 33(a), 33(b) and 33(c) are explanatory diagram illustrating output voltage in the conventional smoke sensor.
Figure 33:
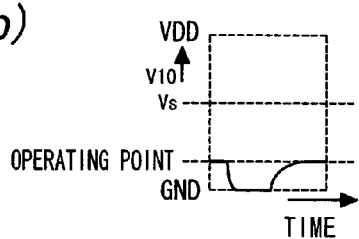
Figure 33:
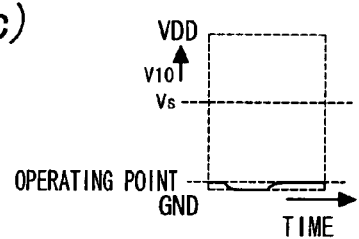

The circuit block 1 comprises a current-voltage conversion circuit and a determination processing section (corresponding to the alarm set-off determination circuit 14 of FIG. 30(b)). The current-voltage conversion circuit converts the input current inputted from the light-receiving section into output voltage the value whereof fluctuates according to the fluctuation of the input current, and outputs the output voltage. The determination processing section determines the presence or absence of smoke in the sensing space on the basis of the output voltage of the current-voltage conversion circuit.

Figure 1:
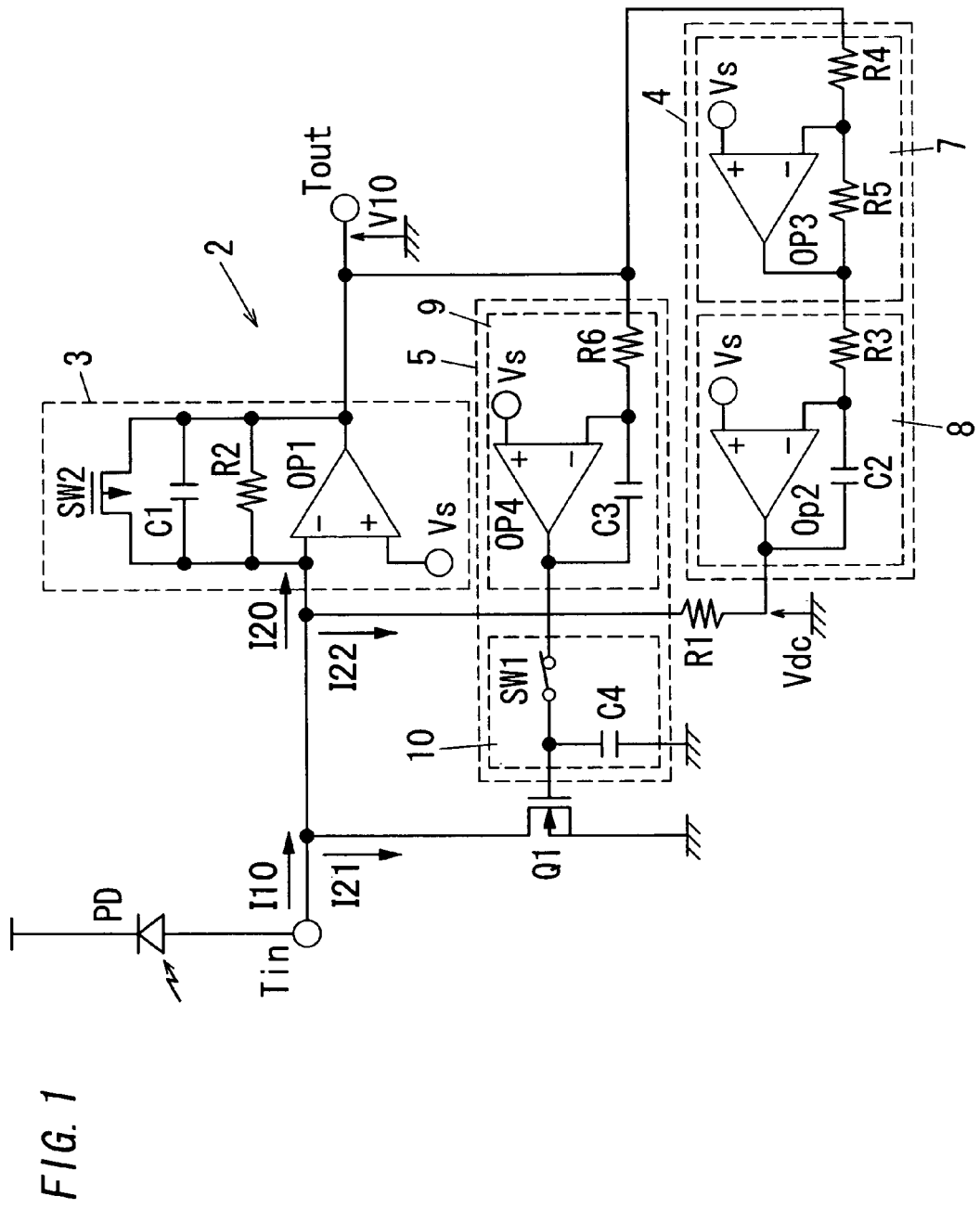
FIG. 1 is a schematic circuit diagram illustrating the configuration of Embodiment 1 of the present invention.
Figure 2:
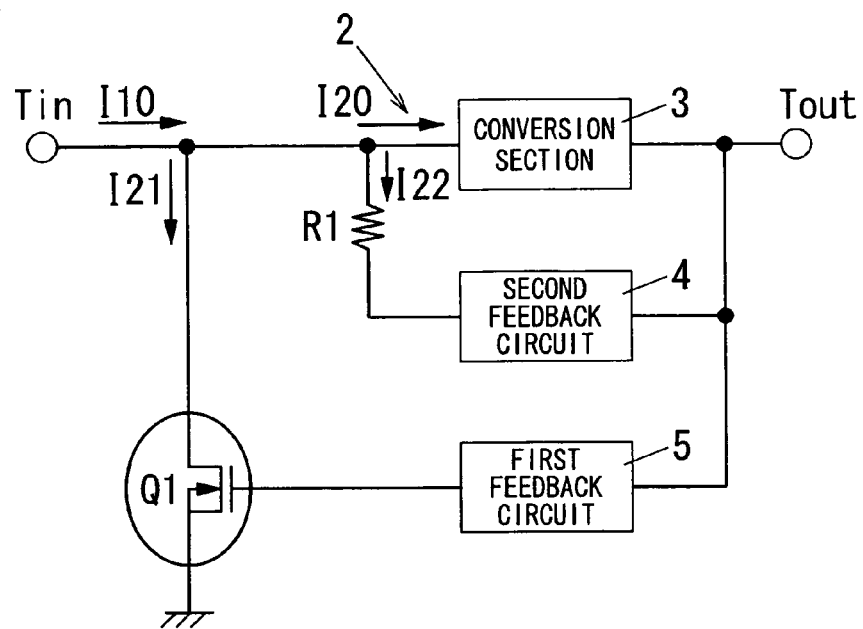
FIG. 2 is a block diagram illustrating the configuration of Embodiment 1.

As illustrated in FIG. 2, a current-voltage conversion circuit 2 comprises a conversion section 3 that converts an input current I20 inputted from a connection terminal Tin to an output voltage V10, and that outputs the output voltage V10 from an output terminal Tout. Further, the current-voltage conversion circuit 2 comprises, as low-frequency correction means, a second feedback circuit 4 and a correcting resistor R1, and a first feedback circuit 5 and a correcting transistor Q1. The second feedback circuit 4 outputs voltage according to the magnitude of a low-frequency component no greater than a predefined second cut-off frequency fc2, of the output voltage V10. A correcting resistor R1 is inserted between the output of the second feedback circuit 4 and a connection terminal Tin of the conversion section 3. The first feedback circuit 5 outputs voltage according to the magnitude of a low-frequency component no greater than a predefined first cut-off frequency fc1, of the output voltage V10. The correcting transistor Q1 is configured in such a way so as extract, from the sensor current I10, current according to the magnitude of the output of the first feedback circuit 5. The sensor current I10 is a supplied by a current source, flows through a photodiode PD (FIG. 1) as a light-receiving section, and has a magnitude according to the light reception intensity of the photodiode PD.

The low-frequency correction means causes the flow of correction currents I21, I22 according to the magnitude of a low-frequency component, and uses the combined current of the correction currents I21, I22 and an input current I20 as a sensor current I10, to reduce thereby the input current I20 by the correction currents I21, I22. The specific configuration of the current-voltage conversion circuit 2 will be explained next with reference to FIG. 1.

As illustrated in FIG. 1, the conversion section 3 comprises an operational amplifier OP1, such that a converting resistor R2 is connected between an output terminal and an inverting input terminal of the operational amplifier OP1, and a reference voltage Vs is applied to a non-inverting input terminal of the operational amplifier OP1. The inverting input terminal of the operational amplifier OP1 functions as an input terminal of the conversion section 3. The photodiode PD, as a light-receiving section, is connected to the above-described connection terminal Tin. The sensor current I10 from the photodiode PD is inputted, from an input terminal (inverting input terminal) to the conversion section 3, via the connection terminal Tin.

The conversion section 3 has a capacitor C1 connected in parallel to the converting resistor R2, and functions also as a low-pass filter. The circuit constant of the converting resistor R2 and the capacitor C1 in the conversion section 3 is set in such a manner that there passes only an input current I20 of a frequency no greater than a predefined cut-off frequency fc0. The cut-off frequency fc0 is represented by $fc0=1/(2\pi \times r2 \times c1)$, using the constant c1 of the capacitor C1 and the resistance value r2 of the converting resistor R2, and is set in such a manner that at least a detection signal is allowed through. Herein, the detection signal refers to the pulsed sensor current I10 generated upon reception, by the photodiode PD, of light from the LED 6 FIGS. 30(a) and 30(b)) as the light-emitting section.

Therefore, the current-voltage conversion circuit 2 uses, as an operating point, the output voltage V10 (herein, reference voltage Vs) in a state where the sensor current I10 from the photodiode PD is zero, and causes the output voltage V10 to fluctuate with reference to the operating point, in accordance with the fluctuation of the sensor current I10.

The second feedback circuit 4 has an inverting amplifier circuit 7 and a second integrating circuit 8. The inverting amplifier circuit 7 inverts and amplifies the output voltage V10 of the conversion section 3. The second integrating circuit 8 integrates the output voltage V10 inverted and amplified by the inverting amplifier circuit 7, and outputs an integration voltage Vdc corresponding to an integration value component of the output voltage V10.

The second integrating circuit 8 comprises an operational amplifier OP2, such that an inverting input terminal of the operational amplifier OP2 is connected to the output of the inverting amplifier circuit 7 via a resistor R3 and a capacitor C2 is connected between the output terminal and the inverting input terminal of the operational amplifier OP2. As a result, the second integrating circuit 8 functions as a low-pass filter having a time constant determined by the resistor R3 and the capacitor C2. The time constant is set in such a manner that the integrating circuit 8 has a second cut-off frequency fc2 for blocking at least the above detection signal (i.e. a frequency that is lower than the frequency of the detection signal).

The inverting amplifier circuit 7 is provided in order to bring the output of the integrating circuit 8 in-phase with respect to the output voltage V10 of the conversion section 3. The inverting amplifier circuit 7 comprises an operational amplifier OP3, such that an inverting input terminal of the operational amplifier OP3 is connected to an output terminal Tout of the conversion section 3 via a resistor R4, and a resistor R5 is connected between the output terminal and the inverting input terminal of the operational amplifier OP3. A reference voltage Vs is applied to the non-inverting input terminals of both operational amplifiers OP2, OP3.

If the detection signal and the low-frequency component are comprised in the input current I20 of the conversion section 3, the integration voltage Vdc outputted by the second integrating circuit 8 becomes a voltage corresponding to the low-frequency component. In this case, the input current I20 is phase-reversed first in the conversion section 3, and is further reversed once at each of the inverting amplifier circuit 7 and the integrating circuit 8. As a result, the integration voltage Vdc, of opposite phase to the input current I20, appears in the output of the integrating circuit 8. Herein, the reference voltage Vs is applied to the connection terminal Tin of the conversion section 3, and hence there arises a potential difference, in which the integration voltage Vdc is subtracted from the reference voltage Vs, between the two ends of the correcting resistor R1. As a result, the correction current I22, corresponding to the magnitude of the integration voltage Vdc, is caused to flow through the correcting resistor R1, whereby the correction current I22 can be extracted from the sensor current I10. That is, in a case where a low-frequency component is comprised in the sensor current I10, the current from which the low-frequency component has been subtracted is inputted, as the input current I20, into the conversion section 3, as a result of which the low-frequency component is removed from the output voltage V10.

The thermal noise of the correcting resistor R1 itself increases, and the input conversion noise of the current-voltage conversion circuit 2 increases as well, if there is used, as the correcting resistor R1, an element having a small resistance value. This is problematic in that, as a result, there drops the SN ratio, which is the ratio between the signal component (sensor current I10) from the photodiode PD, as the detection target, and the above-mentioned noise. Therefore, the resistance value of the correcting resistor R1 is set to be somewhat large.

In the smoke sensor A of the present embodiment, the first feedback circuit 5 has a first integrating circuit 9 and a sample-and-hold-circuit 10. The first integrating circuit 9 integrates the output voltage V10 of the conversion section 3. The sample-and-hold-circuit 10 samples and holds the output of the first integrating circuit 9.

The first integrating circuit 9 comprises an operational amplifier OP4, such that an inverting input terminal of the operational amplifier OP4 is connected to an output terminal Tout via a resistor R6, and a capacitor C3 is connected between the output terminal and the inverting input terminal of the operational amplifier OP4. As a result, the first integrating circuit 9 functions as a low-pass filter having a time constant determined by the resistor R6 and the capacitor C3. The time constant is set in such a manner that the integrating circuit 9 has a first cut-off frequency fc1 that is higher than the second cut-off frequency fc2 of the second integrating circuit 8 (i.e. fc2<fc1). A reference voltage Vs is applied to a non-inverting input terminal of the operational amplifier OP4.

A correcting transistor Q1 is inserted between the connection terminal Tin and ground (predefined potential point). Herein, the correcting transistor Q1 is configured as an N channel MOSFET in such a manner that the correction current I21 according to the output of the first integrating circuit 9 flows from the connection terminal Tin of the conversion section 3 to ground. The correcting transistor Q1 is provided in such a manner that the drain thereof is connected to the connection terminal Tin, the source is connected to ground, and the gate is connected to the output of the integrating circuit 9 (output terminal of the operational amplifier OP4), via the sample-and-hold-circuit 10.

The sample-and-hold-circuit 10 has a capacitor C4 and a normally-closed first switch SW1. The first switch SW1 is inserted between the output of the integrating circuit 9 and the gate of the correcting transistor Q1. The capacitor C4 is connected between the gate of the correcting transistor Q1 and ground. The sample-and-hold-circuit 10 switches off the first switch SW1 at a predefined timing, whereby the output of the integrating circuit 9 is sustained, as the output voltage of the capacitor C4, for the above predefined timing.

Thanks to the above-described configuration, the low-frequency component no greater than the first cut-off frequency fc1, of the output voltage V10 of the conversion section 3, appears in the output of the integrating circuit 9, through integration, by the integrating circuit 9, of the output voltage V10 of the conversion section 3. In this case, the input current I20 is phase-reversed first in the conversion section 3, and is further reversed in the integrating circuit 9. As a result, there appears a low-frequency component, in-phase with the input current I20, in the output of the integrating circuit 9. The output of the integrating circuit 9 is applied to the gate of the correcting transistor Q1 via the sample-and-hold-circuit 10. As a result, a correction current I21 according to the magnitude of the output of the integrating circuit 9 (low-frequency component of the output voltage V10) flows between the drain and source of the correcting transistor Q1, with the switch SW1 of the sample-and-hold-circuit 10 in an on-state. Therefore, a low-frequency component no greater than the first cut-off frequency fc1 and comprised in the sensor current I10 can be extracted to the correcting transistor Q1, and the gain of the low-frequency component can be reduced in the current-voltage conversion circuit 2 as a whole.

When the switch SW1 of the sample-and-hold-circuit 10 is switched off, the output of the integrating circuit 9 is cut off from the gate of the correcting transistor Q1. The output of the integrating circuit 9, however, is sustained as the two-terminal voltage of the capacitor C4. As a result, the correction current I21, according to the magnitude of the output of the integrating circuit 9 immediately before switching-off of the switch SW1, can be caused to continue flowing between the drain and source of the correcting transistor Q1. In other words, when the sample-and-hold-circuit 10 operates, through switching-off of the switch SW1, there drops the upper limit value (first cut-off frequency fc1) of the frequency of the correction current I21 that can flow in the correcting transistor Q1. The DC component can be removed from the output voltage V10 by being extracted next to the correcting transistor Q1.

In the present embodiment, the timing at which the switch SW1 of the sample-and-hold-circuit 10 is switched off is set in accordance with the period at which the LED 6 of the smoke sensor A outputs pulsed light, i.e. the period at which there is detected the presence or absence of smoke flowing in the sensing space (hereafter, sensing period). In the smoke sensor A of the present embodiment, thus, a detection signal generated when the photodiode PD receives light from the LED 6, during the above-mentioned sensing period, is converted into voltage, and is outputted as the output voltage V10. Therefore, the switch SW1 is switched off at the sensing period, in such a manner so as to preclude the detection signal from being extracted to the correcting transistor Q1 during the sensing period.

In a more detailed explanation, the first cut-off frequency fc1 of the first integrating circuit 9 is set to be closer to the frequency of the detection signal than to the second cut-off frequency fc2 of the second integrating circuit 8. As a result, it is possible that, with the switch SW1 in an on state, the detection signal is extracted to the correcting transistor Q1 and that there decreases the gain of the detection signal in the current-voltage conversion circuit 2 as a whole. Therefore, the sample-and-hold-circuit 10 is operated through switching-off of the switch SW1 in the sensing period, whereby the detection signal is prevented from being extracted to the correcting transistor Q1, and the gain of the detection signal is kept high in the current-voltage conversion circuit 2 as a whole.

In case that the smoke sensor A is intermittently driven, as described above, power is supplied to the current-voltage conversion circuit 2 also intermittently, and the above sensing period is set within the period at which power is supplied to the current-voltage conversion circuit 2. The switch SW1 is switched off only during the sensing period. The switch SW1 is switched on from start of power supply to the current-voltage conversion circuit 2 until start of the sensing period, and from the end of the sensing period until discontinuation of power supply to the current-voltage conversion circuit 2.

In the sensing period at which the switch SW1 is switched off, the output of the first feedback circuit 5 is fixed to the value immediately before the switch SW1 is switched off. Therefore, the fluctuation-free DC component comprised in the sensor current I10 can be continuously extracted to the correcting transistor Q1. On the other hand, the low-frequency component having fluctuation and comprised in the sensor current I10 cannot be extracted to the correcting transistor Q1, even if the low-frequency component is no greater than the first cut-off frequency fc1.

In the sensing period, however, the low-frequency component no greater than the second cut-off frequency fc2 can be extracted to the correcting resistor R1 by being removed as the output of the second feedback circuit 4.

In the smoke sensor A having the above-described configuration, the low-frequency component no greater than the first cut-off frequency fc1, of the sensor current I10, is fed back through the first feedback circuit 5 and is extracted to the correcting transistor Q1, during periods other than the sensing period. Therefore, the operating point of the output voltage V10 settles down to the reference voltage Vs even when the sensor current I10 comprises a low-frequency component. In the sensing period, the low-frequency component no greater than the second cut-off frequency fc2, of the sensor current I10, is fed back through the second feedback circuit 4, and is extracted to the correcting resistor R1. Therefore, the operating point of the output voltage V10 settles down to the reference voltage Vs even when the sensor current I10 comprises a low-frequency component. In this case, the switch SW1 is switched off, and the output of the first feedback circuit 5 is held at the value immediately before the sensing period. Therefore, the output voltage V10 corresponding to the detection signal can be outputted without the detection signal being extracted to the correcting transistor Q1.

That is, it becomes possible to extract a greater current component, as compared with a case where the low-frequency component is extracted only by the correcting resistor R1, through the use of the correcting transistor Q1 and the correcting resistor R1 as means for extracting the low-frequency component comprised in the sensor current I10. At periods other than the sensing period, moreover, the low-frequency component can be removed from the output voltage V10, over a comparatively wide range, through setting a high first cut-off frequency fc1. Also, switching-on and -off the switch SW1 of the sample-and-hold-circuit 10 during the sensing period allows preventing attenuation of the detection signal that is the detection target.

The first cut-off frequency fc1 of the first feedback circuit 5 is set higher than the second cut-off frequency fc2 of the second feedback circuit 4. As a result, the output of the first feedback circuit 5 responds ahead of that of the second feedback circuit 4, when power starts to be supplied to the current-voltage conversion circuit 2. As a result, most of the low-frequency component no greater than the first cut-off frequency fc1 can be extracted to the correcting transistor Q1, without supplementary means or the like for shutting off the second feedback circuit 4. This allows reducing the size of the current-voltage conversion circuit 2.

Moreover, the output of the integrating circuit 9 is cut off from the correcting transistor Q1 in the sensing period, through the use of the sample-and-hold-circuit 10 as frequency switching means that lowers the first cut-off frequency fc1 of the first feedback circuit 5 during the sensing period. This allows advantageously increasing the SN ratio, without the input current I20 being influenced by noise (flicker noise or the like) generated in the integrating circuit 9.

In a specific example of the current-voltage conversion circuit 2 having the above configuration, the first cut-off frequency fc1 of the first feedback circuit 5 is set higher than at least 120 Hz. As a result, the output voltage V10 of the current-voltage conversion circuit 2 does not fluctuate even when influenced by flicker of the light from a fluorescent lamp that is lighted by a commercial power source (60 Hz AC power source) using a Cu—Fe ballast in a case where the photodiode PD receives light from such a fluorescent lamp. The second cut-off frequency fc2 of the second feedback circuit 4 is also set higher than 120 Hz. As a result there is fed back, through the second feedback circuit 4, a low-frequency component no greater than 120 Hz, influenced by the light from the fluorescent lamp, in such a manner that the low-frequency component is extracted to the correcting resistor R1, also during the sensing period at which the switch SW1 is switched off.

In FIG. 1, the second switch SW2 is provided and is connected in parallel to the converting resistor R2 of the conversion section 3. The switch SW2 is a normally-closed switch that is switched off at the same timing as the first switch SW1 and that has the below-described function.

Figure 3A:
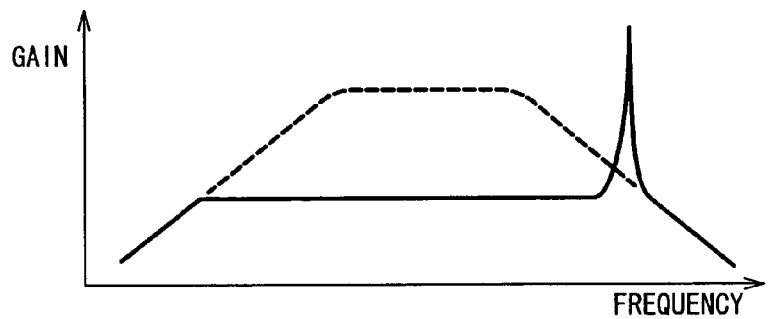
FIGS. 3(a) and 3(b) are characteristic diagram illustrating the gain of a current-voltage conversion circuit of Embodiment 1.
Figure 4:
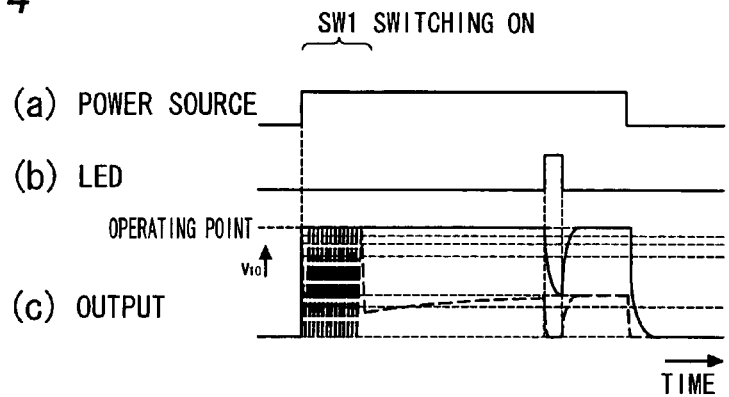
FIG. 4 is a timing chart illustrating the operation of Embodiment 1.

If, hypothetically, only the first switch SW1 is provided, then the cut-off frequency fc1 of the first feedback circuit 5 shifts to a high frequency-side when the first switch SW1 is switched on. As a result, there collapses the gain on the low-frequency side, denoted by the solid line in the gain frequency characteristic of the current-voltage conversion circuit 2 as a whole, illustrated in FIG. 3(a), when the first switch SW1 is switched on. A gain peak accordingly appears between the cut-off frequency fc0 and the first cut-off frequency fc1, and system oscillation becomes likelier, i.e. the output voltage V10 is likelier to oscillate. This is problematic in that, as a result, the rise in the output voltage V10 becomes delayed when the first switch SW1 is switched off at a time where the output voltage V10 is low, as indicated by the broken line of (c) in FIG. 4.

Figure 3B:
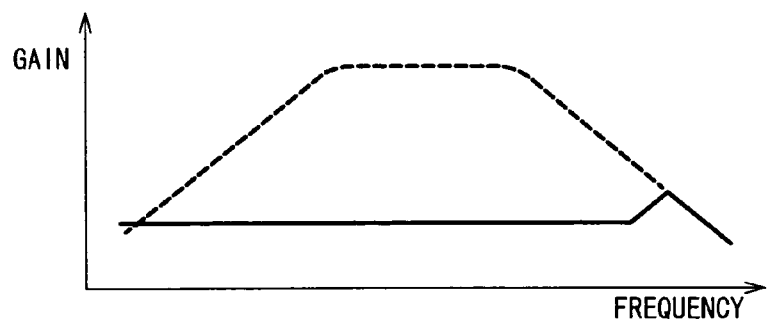

In the present embodiment, by contrast, the second switch SW2 is connected in parallel to the converting resistor R2. As a result, the gain of the conversion section 3 collapses through connection between both ends of the converting resistor R2, as illustrated in FIG. 3(b), during the time at which the first switch SW1 is switched on, through switching-on of the second switch SW2 together with the first switch SW1, from the time at which the power source is turned on until the start of the sensing period. This allows canceling the above-described gain peak, and allows suppressing system oscillation caused by switching-on of the first switch SW1.

In the present embodiment, moreover, the circuits used as the integrating circuits 8, 9 of the first and second feedback circuits 4, 5 are not passive circuits but active circuits having the operational amplifiers OP2, OP4. As a result, the first and second feedback circuits 4, 5 can have high gain towards low-frequency components, and feedback can be performed up to the open gain of the operational amplifiers OP2, OP4. In a configuration using passive filters, specifically, the output voltage V10 suffers a voltage drop (the amount of voltage drop varies depending on the gain) when the first feedback circuit 5 is operated. When the sample-and-hold-circuit 10 is operated thereafter, the output voltage V10 fluctuates likewise upon operation of the second feedback circuit 4. This fluctuation appears eventually in the final output. Therefore, the detection signal may be erroneous during such fluctuations. Conceivably, the operation of the sample-and-hold-circuit 10 could be discontinued immediately prior to the timing at which the detection signal is generated, with a view to suppressing the above fluctuation. However, this would entail a greater current consumption in the circuit as a whole. By contrast, active filters are used in the present embodiment, and hence there can be prevented drops of the output voltage V10 due to the low-frequency component, while saturation of the output voltage V10 can likewise be reliably avoided.

Preferably, the power source voltage of the first feedback circuit 5 is higher than the power source voltage of circuits in the current-voltage conversion circuit 2 other than the feedback circuit 5. This allows increasing the output voltage of the first feedback circuit 5 (i.e. the gate voltage of the correcting transistor Q1), and allows, therefore, extracting a comparatively large correction current I21 in the correcting transistor Q1. This is advantageous in that, as a result, the low-frequency component can be removed from the output voltage V10 also when the sensor current I10 comprises a low-frequency component of comparatively large amplitude, and there can be set a yet greater upper limit for the magnitude of the low-frequency component whose influence on the output voltage V10 can be suppressed.

In some cases, the gate voltage of the correcting transistor Q1 decreases gradually over time due to the influence of leakage current that occurs between ground and the gate of the correcting transistor Q1, also during the sensing period at which the sample-and-hold-circuit 10 is working. In such cases, the correction current I21 extracted between the drain and the source of the correcting transistor Q1 decreases also gradually and hence the output voltage V10 may fluctuate in response thereto. As a countermeasure, there could conceivably be used, in the first switch SW1, an element (for instance, analog switch) whose off-resistance is smaller than the resistance value between the gate and the source of the correcting transistor Q1. This would allow, as a result, suppressing the drop of gate voltage due to the leakage current, and suppressing fluctuation of the output voltage V10, thanks to the small current that would flow via the off-resistance of the switch SW1, also during the sensing period at which the switch SW1 is switched off.

Figure 5:
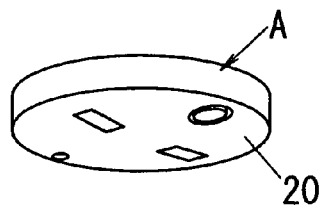
FIG. 5 is a perspective-view diagram illustrating a smoke sensor of Embodiment 1.

As described above, in the smoke sensor A of the present embodiment the influence of the low-frequency component on the output voltage V10 can be suppressed also when the sensor current I10 comprises a large low-frequency component that arises from incidence of strong ambient light onto the photodiode PD. Accordingly, the labyrinth 21 can be simplified, and, for instance, the smoke sensor A can be made thinner, as illustrated in FIG. 5. The smoke sensor A of FIG. 5, has a sensing space in front of the housing 20 (below the housing 20, when the latter is affixed to the ceiling) and detects smoke when the photodiode PD receives light, from the LED 6, that is diffused and reflected by smoke that flows into the sensing space.

Embodiment 2

Figure 6:
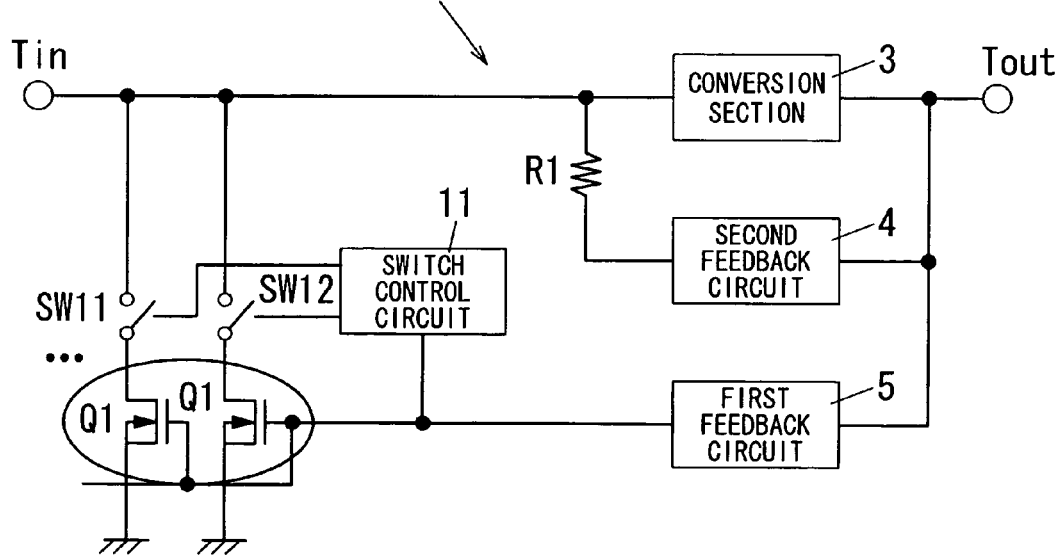
FIG. 6 is a schematic circuit diagram illustrating the configuration of Embodiment 2 of the present invention.

The smoke sensor A of the present embodiment differs from the smoke sensor A of Embodiment 1 in that now there is provided a plurality of correcting transistors Q1, as illustrated in FIG. 6.

In the present embodiment, specifically, a plurality of correcting transistors Q1 is connected in parallel between a connection terminal Tin and ground (predefined potential point), such that the output of the first feedback circuit 5 is connected to the gate of each correcting transistor Q1. Selection switches SW11, SW12, . . . are inserted into connections, respectively, each of which is a connection between the connection terminal Tin and the drain of each correcting transistor Q1, such that a switch control circuit 11 controls the switching on-off of the selection switches SW11, SW12, . . . .

The switch control circuit 11 is configured in such a way so as monitor the output of the first feedback circuit 5 that is applied to the gates of the correcting transistors Q1. The switch control circuit 11 controls the switching-on and -off of the selection switches SW11, SW12, . . . in accordance with the magnitude of the output of the feedback circuit 5, in such a manner that the greater the output of the feedback circuit 5 is, the more selection switches SW11, SW12, . . . are switched on. Therefore, the number of correcting transistors Q1 connected in parallel between the connection terminal Tin and ground, as well as the number of correcting transistors Q1 used for current extraction, increases as the correction current I21 extracted from the sensor current I10 becomes greater.

The ratio (W/L) between channel width (W) and channel length (L) must be increased in order to increase the current value that can be coped with by the correcting transistors Q1 that extracts correction current I21 from the sensor current I10. However, an increase of the above ratio (W/L) entails greater thermal noise in the correcting transistors Q1, even if the amount of extracted current stays the same. The present embodiment, by contrast, is advantageous in that comparatively large currents can be coped with, while keeping both thermal noise and the above ratio (W/L) small, by connecting in parallel a plurality of correcting transistors Q1 when the comparatively large currents is extracted.

Other features and functions are identical to those of Embodiment 1.

Embodiment 3

Figure 7:
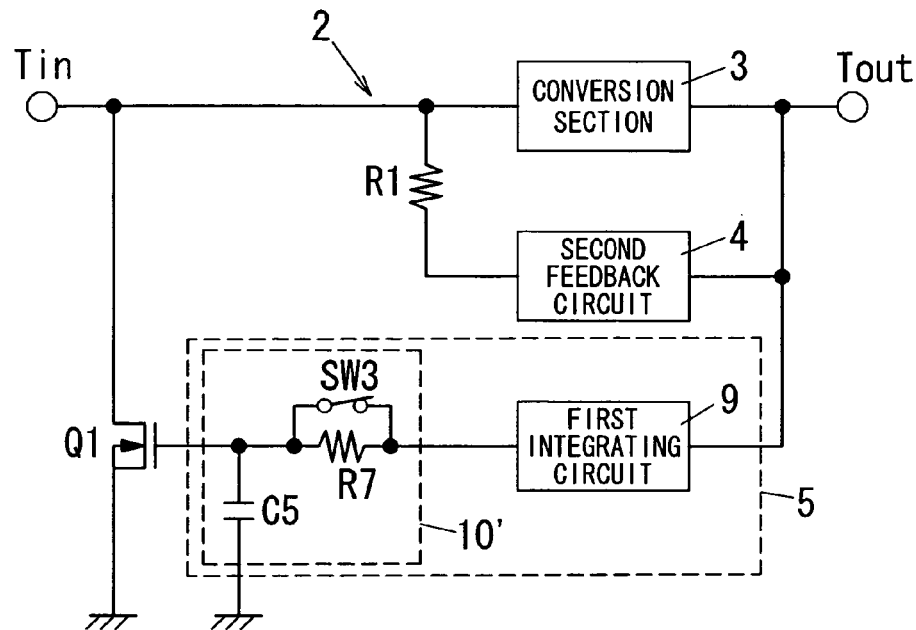
FIG. 7 is a schematic circuit diagram illustrating the configuration of Embodiment 3 of the present invention.

A smoke sensor A of the present embodiment differs from the smoke sensor A of Embodiment 1 in that now a low-pass filter circuit 10' is provided, as illustrated in FIG. 7, instead of the sample-and-hold-circuit 10, as frequency switching means that switches the first cut-off frequency fc1 of the first feedback circuit 5.

The low-pass filter circuit 10' comprises a resistor R7, a capacitor C5 and a normally-closed third switch SW3. The resistor R7 is inserted between the output of the first integrating circuit 9 and the gate of the correcting transistor Q1. The capacitor C5 is connected between the gate of the correcting transistor Q1 and ground. The third switch SW3 is connected in parallel to the resistor R7. The low-pass filter circuit 10' lets through a low-frequency component that is no greater than a predefined cut-off frequency determined by the resistor R7 and the capacitor C5.

In the above configuration, the output of the integrating circuit 9 is directly applied to the correcting transistor Q1 when the third switch SW3 is in an on state. When the third switch SW3 is in an off state, by contrast, the output of the integrating circuit 9 is applied to the correcting transistor Q1 via the low-pass filter circuit 10'. Therefore, the first cut-off frequency fc1 of the first feedback circuit 5 is lowered through switching-off of the third switch SW3.

In the present embodiment, the timing at which the switch SW3 of the low-pass filter circuit 10' is switched off is set in accordance with the period at which the LED 6 of the smoke sensor A outputs pulsed light (sensing period). That is, the switch SW3 is switched off at the sensing period, in such a manner so as to preclude the detection signal from being extracted to the correcting transistor Q1 during the sensing period.

Other features and functions are identical to those of Embodiment 1.

Embodiment 4

Figure 8:
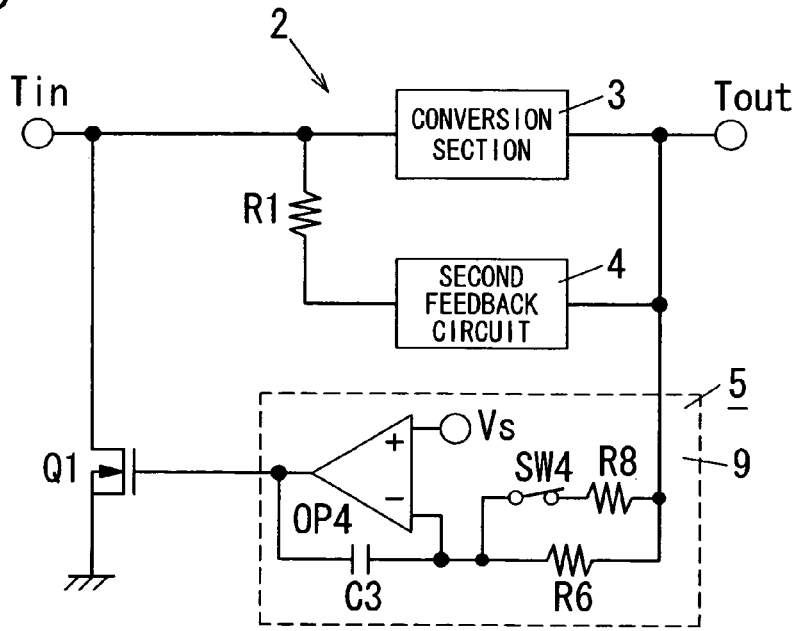
FIG. 8 is a schematic circuit diagram illustrating the configuration of Embodiment 4 of the present invention.

The smoke sensor A of the present embodiment differs from the smoke sensor A of Embodiment 1 in that now a series circuit of a second resistor R8 and a fourth switch SW4 is provided, instead of the sample-and-hold-circuit 10, as the frequency switching means, as illustrated in FIG. 8.

The series circuit of the resistor R8 and normally-closed fourth switch SW4 is connected in parallel to the first resistor R6 of the first integrating circuit 9. As a result, when the fourth switch SW4 is in an on state, the first cut-off frequency fc1 of the integrating circuit 9 is determined by a time constant that is in turn determined by the resistor R6, the resistor R8 and the capacitor C3. By contrast, when the fourth switch SW4 is in an off state, the first cut-off frequency fc1 of the integrating circuit 9 is determined by a time constant that is in turn determined by the resistor R6 and the capacitor C3. Therefore, the first cut-off frequency fc1 of the first feedback circuit 5 is lowered through switching-off of the fourth switch SW4.

In present embodiment, the timing at which the switch SW4 of the first integrating circuit 9 is switched off is set in accordance with the period at which the LED 6 of the smoke sensor A outputs pulsed light (sensing period). That is, the switch SW4 is switched off at the sensing period, in such a manner so as to preclude the detection signal from being extracted to the correcting transistor Q1 during the sensing period.

Other features and functions are identical to those of Embodiment 1.

Embodiment 5

Figure 9:
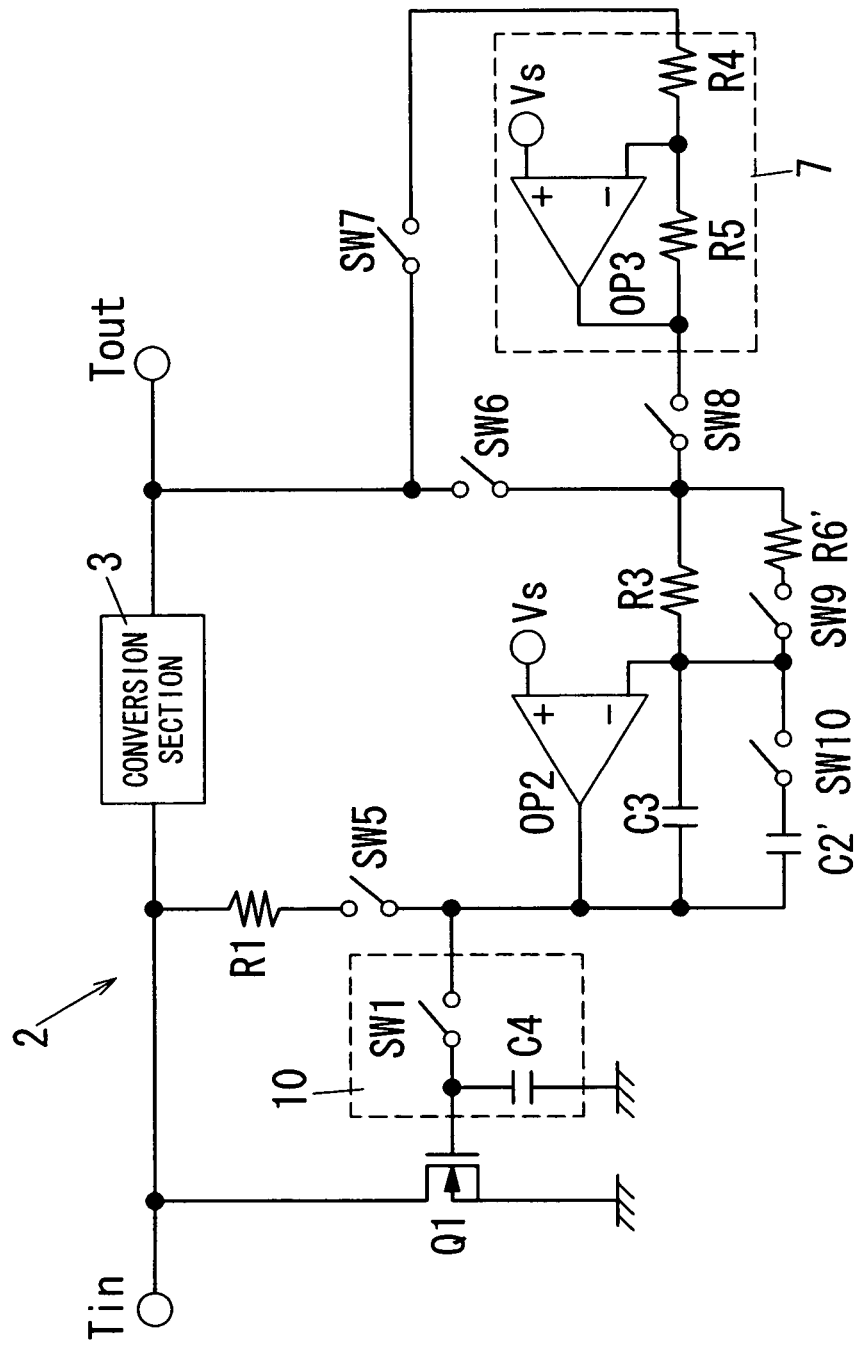
FIG. 9 is a schematic circuit diagram illustrating the configuration of Embodiment 5 of the present invention.

The smoke sensor A of the present embodiment differs from the smoke sensor A of Embodiment 1 in that now the second feedback circuit 4 and the first feedback circuit 5 double as one operational amplifier OP2, as illustrated in FIG. 9.

In the present embodiment, specifically, the operational amplifier OP2 of the second feedback circuit 4 doubles as the first feedback circuit 5. The smoke sensor A comprises a plurality of switches (mode switching means) SW5 to SW10 for switching between an operation mode of operating the second feedback circuit 4, and an operation mode of operating the first feedback circuit 5. In a more detailed explanation, a switch SW5 is inserted between the correcting resistor R1 and the output terminal of the operational amplifier OP2. A switch SW6 is inserted between the output terminal Tout and the resistor R3. A switch SW7 is inserted between the output terminal Tout and the input (resistor R4) of the inverting amplifier circuit 7. A switch SW8 is inserted between the resistor R3 and the output of the inverting amplifier circuit 7. Further, a series circuit comprising a resistor R6' and a switch SW9 is connected in parallel to the resistor R3 that is connected to the inverting input terminal of the operational amplifier OP2. The capacitor C3 is connected between the output terminal and the inverting input terminal of the operational amplifier OP2. A series circuit comprising the capacitor C2' and a switch SW10 is connected in parallel to the capacitor C3.

Figure 10:
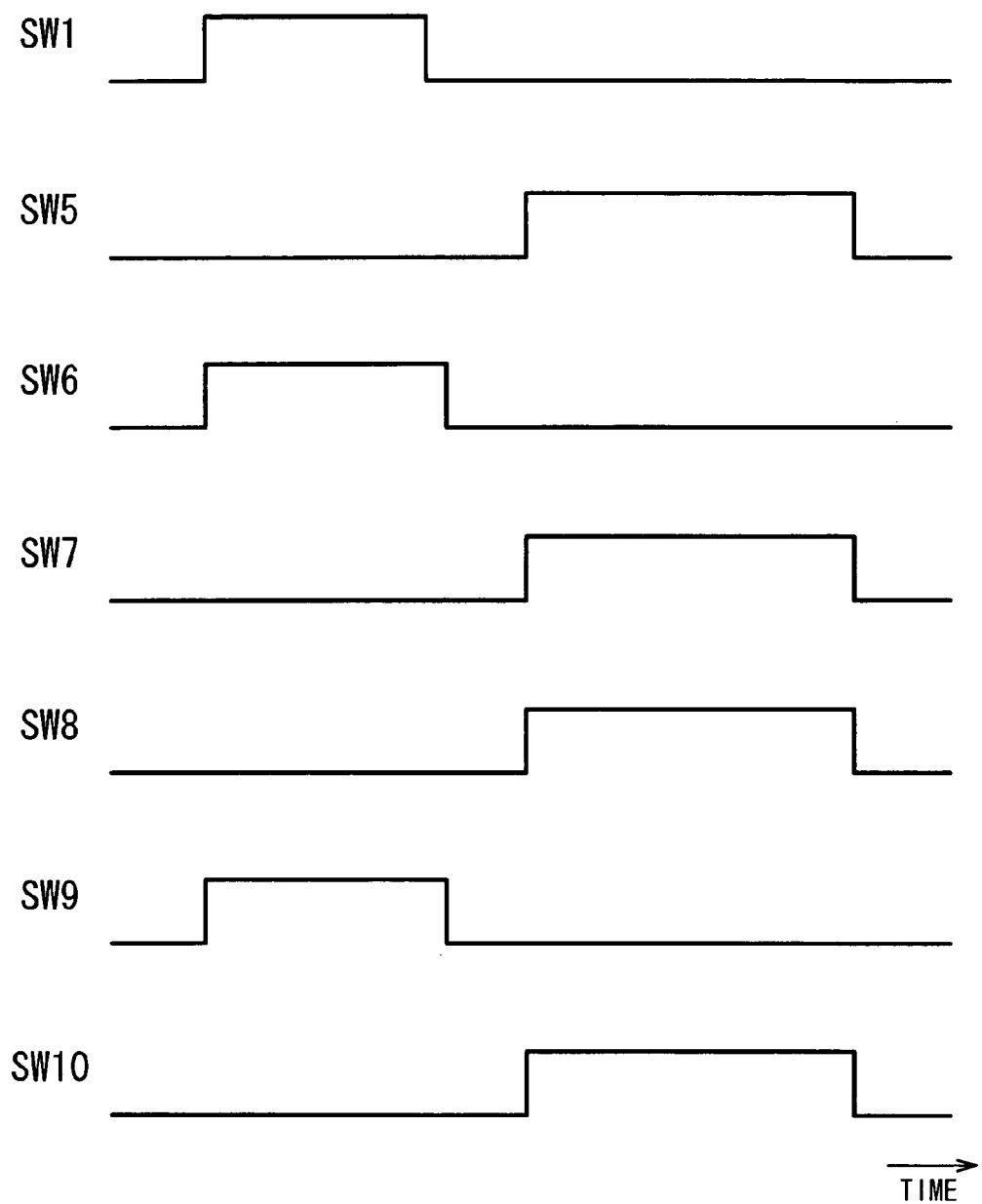
FIG. 10 is a timing chart illustrating the operation of Embodiment 5.

As illustrated in FIG. 10, the first feedback circuit 5 is operated through switching-on of the switches SW6, SW9 simultaneously with the first switch SW1, as illustrated in FIG. 10. The other switches SW5, SW7, SW8, SW10 are switched off at this time. In this state, the output terminal Tout is connected to the inverting input terminal of the operational amplifier OP2 via a parallel circuit of the resistor R3 and the resistor R6', and the output terminal of the operational amplifier OP2 is connected to the gate of the correcting transistor Q1. Further, the capacitor C3 is connected between the output terminal and the inverting input terminal of the operational amplifier OP2.

The second feedback circuit 4 is operated through simultaneous switching-on of the switches SW5, SW7, SW8, SW10, as illustrated in FIG. 10. The other switches SW1, SW6, SW9 are switched off at this time. In this state, the output terminal Tout is connected to the inverting input terminal of the operational amplifier OP2 via the inverting amplifier circuit 7 and the resistor R3, and the output terminal of the operational amplifier OP2 is connected to the correcting resistor R1. Further, a parallel circuit of the capacitor C3 and the capacitor C2' is connected between the output terminal and the inverting input terminal of the operational amplifier OP2.

Thus, although the inverting amplifier circuit OP2 constitutes an integrating circuit in both states, the cut-off frequency of the inverting amplifier circuit OP2 is different in either state. With the switches SW1, SW6, SW9 in the on state, specifically, the cut-off frequency is set to the first cut-off frequency fc1 by the capacitor C3 and the parallel circuit comprising the resistor R3 and the resistor R6'. With the switches SW5, SW7, SW8, SW10 in the on state, by contrast, the cut-off frequency is set to the second cut-off frequency fc2 by the resistor R3 and the parallel circuit comprising the capacitor C3 and the capacitor C2'.

In the above-described configuration of the present embodiment, the operational amplifier OP2 is used in both the second feedback circuit 4 and the first feedback circuit 5. This allows, as a result, reducing size and power consumption as compared with a case in which separate operational amplifiers are respectively provided in the feedback circuits 4, 5.

Other features and functions are identical to those of Embodiment 1.

The above embodiments have been explained assuming a configuration wherein the sensor current I10 flows from the photodiode PD to the connection terminal Tin, when the photodiode PD receives light. The embodiments, however, are not limited to that configuration, which may also be one wherein the orientation of the sensor current I10 with respect to the connection terminal Tin is reversed, so that the sensor current I10 flows from the connection terminal Tin to the photodiode PD, when the photodiode PD receives light. In this case, the current-voltage conversion circuit 2 functions as a current source that supplies the sensor current I10 to the photodiode PD.

Figure 11:
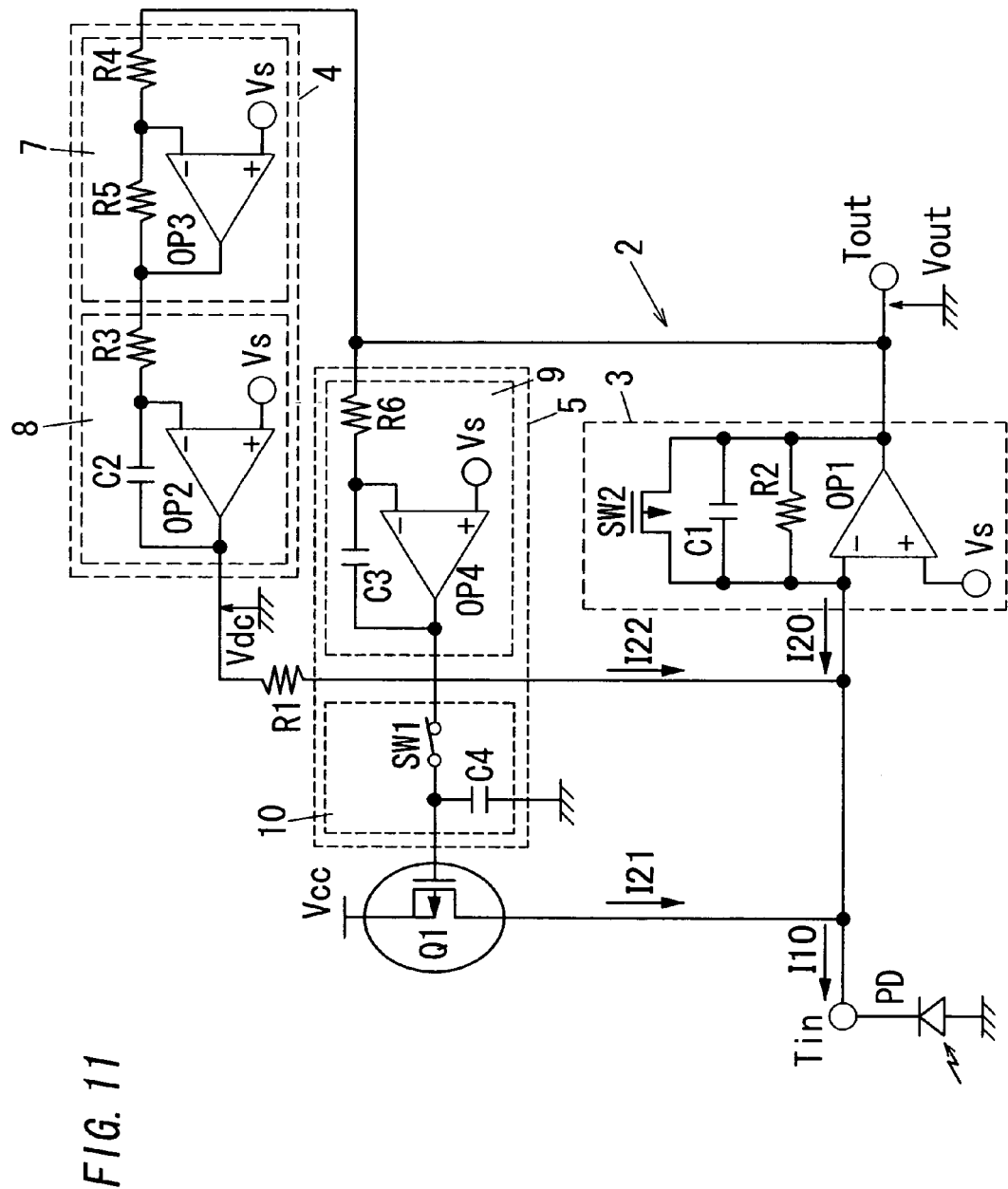
FIG. 11 is a schematic circuit diagram illustrating another configuration of Embodiment 5.

In this case, specifically, the current-voltage conversion circuit 2 has a circuit configuration such as the one illustrated in FIG. 11. Herein, the correcting transistor Q1 comprises a P channel MOSFET connected between the connection terminal Tin and a predefined potential point Vcc, and is configured in such a manner that the correction current I21 according to the output of the first feedback circuit 5 flows from the predefined potential point Vcc to the connection terminal Tin. As a result, the correcting resistor R1 and the correcting transistor Q1 do not function so as to extract the correction currents I21, I22 from the photodiode PD, but so as to supply the correction currents I21, I22 to the photodiode PD.

In a smoke sensor A having the configuration of FIG. 11, the low-frequency component, of the sensor current I10, no greater than the first cut-off frequency fc1 is fed back as the correction current I21 through the correcting transistor Q1 in periods other than the sensing period. Accordingly, the correction current I21 flows into the photodiode PD, in addition to the input current I20 of the conversion section 3. In the sensing period, the low-frequency component, of the sensor current I10, no greater than the second-cut-off frequency fc2 is fed back as the correction current I22 through the correcting resistor R1. Accordingly, the correction current I22 flows into the photodiode PD, in addition to the input current I20 of the conversion section 3.

In the configuration of FIG. 11 as well, thus, the low-frequency correction means causes the flow of the correction current I21, I22, and uses the combined current of the correction currents I21, I22 and the input current I20 as the sensor current I10, whereby the input current I20 can be reduced by the correction currents I21, I22.

In the example of FIG. 11, the P channel MOSFET used as the correcting transistor Q1 has a lower hole mobility than an N channel MOSFET. Therefore, the noise component coming out of the correcting transistor Q1 is smaller than in a case where an N channel MOSFET is used as the correcting transistor Q1. In particular, it is known that flicker noise, caused by capture and release of electrons in dangling bonds at a Si/SiO2 interface, can be lowered in P channel MOSFETs to about ⅓ that of N channel MOSFETs. Therefore, using a P channel MOSFET as the correcting transistor Q1 is effective in enhancing the SN ratio.

In the embodiments above, a photodiode PD has been exemplified as the light-receiving section. The embodiments, however, are not limited to such an example. For instance, CdS or an element such as a thermistor or the like can be used in the light-receiving section. That is, the smoke sensor A of the present invention can be used with a light-receiving section that comprises not only an element that generates photoelectromotive force on its own, such as the photodiode PD, but also a passive element that does not generate a photoelectromotive force on its own, such as CdS or a thermistor.

Embodiment 6

A smoke sensor A of the present embodiment has a sensing space in a housing 20. Further, the smoke sensor A has a light-emitting section, a light-receiving section and a circuit block 30. The light-emitting section intermittently outputs pulsed light towards the sensing space. The light-receiving section is disposed at a position at which direct light from the light-emitting section is not incident, and converts received light into current. The circuit block 30 is configured in such a manner so as to detect smoke in the sensing space, on the basis of an input current from the light-receiving section. When smoke flows into the sensing space in the smoke sensor A, the light from the light-emitting section is diffused and reflected by the smoke in the sensing space, as a result of which there increases the amount of light from the light-emitting section received at the light-receiving section, and there increases the amount of current outputted by the light-receiving section. In the smoke sensor A exemplified herein, a battery is used as a power source. Driving is performed intermittently in order to curb average power consumption and to prolong battery life.

Figure 12:
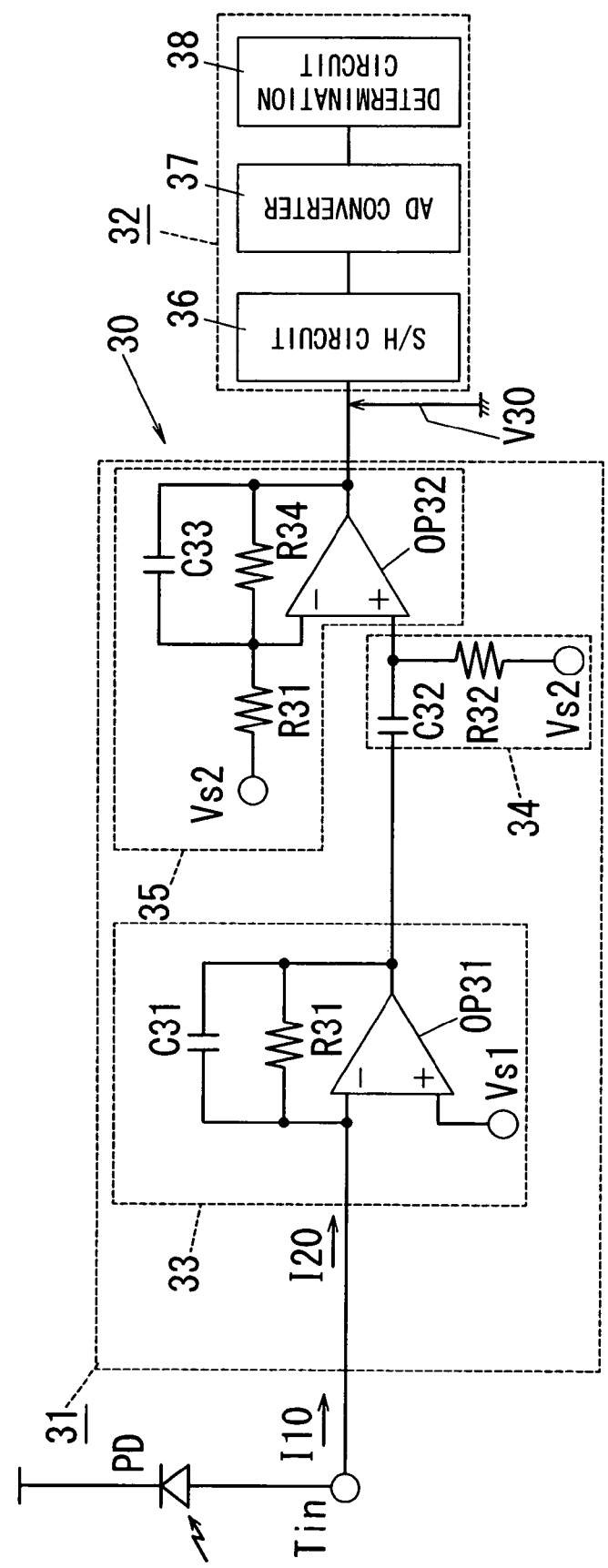
FIG. 12 is a schematic circuit diagram illustrating the configuration of Embodiment 6 of the present invention.

A circuit block 30 of the present embodiment comprises a sensor output processing section 31 and an operation processing section 32, as illustrated in FIG. 12. The sensor output processing section 31 converts the sensor current I10 inputted from the light-receiving section into an output voltage V30, whose voltage value fluctuates in accordance with the fluctuation of the sensor current I10, and outputs the output voltage V30. The operation processing section 32, which is provided after the sensor output processing section 2, determines the presence or absence of smoke in the sensing space on the basis of the output voltage V30. The sensor current I10 is a current, supplied from a current source, that flows through the photodiode PD, as a light-receiving section, and that has a magnitude according to the light reception intensity of the photodiode PD.

The sensor output processing section 31 comprises a current-voltage conversion circuit 33 that converts the input current I20 inputted from the connection terminal Tin to an output voltage, and that outputs the output voltage, as illustrated in FIG. 12. The sensor output processing section 31 further has a high-pass filter 34 connected to the output of the current-voltage conversion circuit 33, and a voltage amplifying circuit 35 that amplifies the output voltage that passes through the high-pass filter 34.

The current-voltage conversion circuit 33 comprises an operational amplifier OP31. A converting resistor R31 is connected between an output terminal and an inverting input terminal of the operational amplifier OP31. The current-voltage conversion circuit 33 is configured in such a manner that a reference voltage Vs1 is applied to a non-inverting input terminal of the operational amplifier OP31. The inverting input terminal of the operational amplifier OP31 functions as an input terminal of the current-voltage conversion circuit 33. The photodiode PD, as a light-receiving section, is connected to the above-described connection terminal Tin. The sensor current I10 from the photodiode PD is inputted, from an input terminal (inverting input terminal) to the current-voltage conversion circuit 33, via the connection terminal Tin.

The current-voltage conversion circuit 33 of the present embodiment has a capacitor C31 connected in parallel to a converting resistor R31, and functions also as a low-pass filter. The circuit constant of the converting resistor R31 and the capacitor C31 in the current-voltage conversion circuit 33 is set in such a manner that there passes an input current I20 of a frequency no greater than a predefined cut-off frequency fc0. The cut-off frequency fc0 is represented by fc0=1/(2π× r31×c31), using the constant c31 of the capacitor C31 and the resistance value r31 of the converting resistor R31, and is set in such a manner that at least a detection signal is allowed through. Herein, the detection signal refers to the pulsed sensor current I10 generated upon reception, by the photodiode PD, of light from the LED 6 (see FIG. 11) as the light-emitting section.

The current-voltage conversion circuit 33 functions also as an integrating circuit having the above-described configuration. Upon fluctuation of the input current I20, therefore, the voltage value of the current-voltage conversion circuit 33 is changed over time, from the point in time at which the input current I20 changes, in such a manner that the output voltage fluctuates with a predefined time delay.

The high-pass filter 34 comprises a series circuit of a capacitor C32 and a resistor R32. This series circuit is connected to an output terminal of the operational amplifier OP31. A reference voltage Vs2 is applied to an end (one end of the resistor R32) of the series circuit, on the opposite side of the operational amplifier OP31. The output of the high-pass filter 34 is outputted from a connecting point of the capacitor C32 and the resistor R32. A cut-off frequency fc31 of the high-pass filter 34 is represented by fc31=1/(2π×r32× c32), using a resistance value r32 of the converting resistor R32 and a constant c32 of the capacitor C32. The cut-off frequency fc31 is set in such a way so as let through at least pulsed output voltage that is generated when the photodiode PD receives light from the LED 6.

The voltage amplifier circuit 35 comprises an operational amplifier OP32 and is configured through connection of a non-inverting input terminal of the operational amplifier OP32 to an output end (connecting point between the capacitor C32 and the resistor R32) of the high-pass filter 34. Further, the voltage amplifying circuit 35 applies the reference voltage Vs2 to the inverting input terminal of the operational amplifier OP32, via the resistor R33, and is configured through connection of a parallel circuit comprising a resistor R34 and a capacitor C33, between the inverting input terminal and the output terminal. The voltage amplified by the voltage amplifying circuit 35 is outputted, as output voltage V30, to the subsequent operation processing section 32.

By virtue of the above configuration, the sensor output processing section 31 causes the output voltage V30 to fluctuate with reference to the operating point, in accordance with the fluctuation of the sensor current I10, using, as the operating point, an instantaneous value of the output voltage V30, with the sensor current I10 from the photodiode PD in a zero state. Herein, the instantaneous value of the output voltage V30 fluctuates transiently in accordance with the fluctuation amount of the input current I20.

The operation processing section 32 comprises a sample-and-hold-circuit (S/H circuit) 36, an AD converter 37 and a determination circuit 38. The sample-and-hold-circuit (S/H circuit) 36 holds an instantaneous value of the output voltage V30 inputted by the sensor output processing section 31. The AD converter 37 functions as detection means that converts the output voltage V30 inputted by the sensor output processing section 31 into a digital value. The determination circuit 38 functions as determination means that determines the presence or absence of smoke in the sensing space, on the basis of the output (digital value) of the AD converter 37.

The AD converter 37 samples and quantizes the output voltage V30, to detect thereby, in the form of a digital value, the instantaneous value of the output voltage V30 at the sampling timing. Sampling is performed twice for each light emission by the LED 6. This allows removing the fluctuation component of the output voltage V30 caused by reception, by the photodiode PD, of light from the LED 6.

In the AD converter 37, specifically, sampling is performed a first time at a first sampling timing set to immediately after emission by the LED 6, and the instantaneous value of the output voltage V30 at this point in time is quantized as a first measurement value. At a second sampling timing set to a predefined time after the first sampling timing, the sample-and-hold-circuit 8 holds the instantaneous value of the output voltage V30, and, in this state, the AD converter 37 performs a second sampling. As a result, the AD converter 37 quantizes, as a second measurement value, the instantaneous value of the output voltage V30 at the point in time of the second sampling timing.

The instantaneous value of the output voltage V30 changes, with a predefined time delay, upon reception, by the photodiode PD, of pulsed light from the LED 6. Therefore, the first sampling timing and second sampling timing are set to a transient response period of the output voltage V30 for the input current I20, in such a manner that at least the instantaneous value change is reflected between the first measurement value and the second measurement value.

Figure 13:
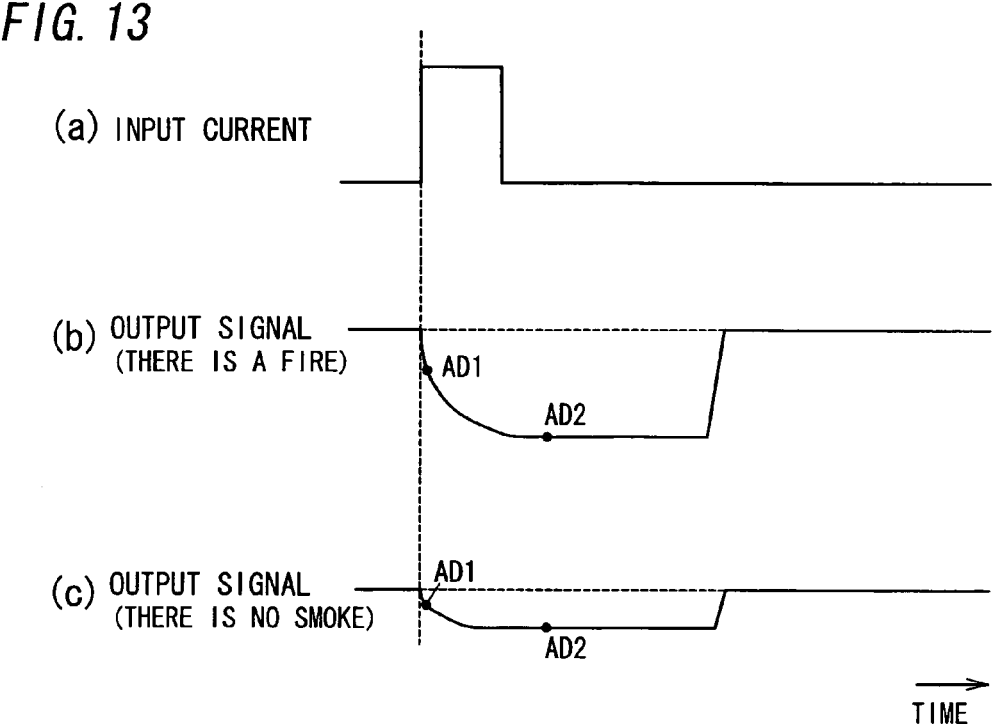
FIG. 13 is a time chart illustrating the operation of Embodiment 6.

In case that the LED 6 is caused to emit light in pulses, as illustrated in (a) of FIG. 13, the output voltage V30 exhibits a comparatively large fluctuation from the first sampling timing to the second sampling timing, as illustrated in (b) of FIG. 13 when smoke flows into the sensing space in an amount greater than a predefined amount. As a result, there arise a comparatively large difference between a first measurement value AD1 and a second measurement value AD2 obtained by the AD converter 37. By contrast, if no smoke flows into the sensing space in an amount greater than a predefined, the output voltage V30 does not exhibit any large fluctuation from the first sampling timing to the second sampling timing, as illustrated in (c) of FIG. 13. Therefore, the difference between the first measurement value AD1 and the second measurement value AD2 obtained by the AD converter 37 is not as large as that of (b) of FIG. 13.

The determination circuit 38 comprises a storage section (not shown) that stores the first and second measurement values obtained by the AD converter 37. Further, the determination circuit 38 comprises an operation section (not shown) that obtains the difference between the first measurement value and the second measurement value stored in the storage section, and determines the presence or absence of smoke in the sensing space by comparing the difference value with a predefined threshold value (hereafter, fire determination level). When in the operation section the difference between the first and second measurement values AD1, AD2 is equal to or greater than the fire determination level, as in (b) of the above-described FIG. 13, it is determined that there is smoke (smoke concentration is reached that can be considered as that of a fire). By contrast, when the difference between the first and second measurement values AD1, AD2 is smaller than the fire determination level, as illustrated in (c) of FIG. 13, it is determined that there is no smoke (smoke concentration is not reached that can be considered as that of a fire).

The determination results by the determination circuit 38 are forwarded to an alarm set-off circuit 15 (see FIGS. 30($a$) and 30($b$)), and a warning is issued, using an appropriate method, upon fire occurrence (i.e. upon determining that smoke is present). The smoke sensor A may also be configured in such a manner that the above determination result is sent to an external device such as a home information panel or the like.

In the above-described configuration, the presence or absence of smoke is determined on the basis of the difference between the instantaneous value of the output voltage V30 at the first sampling timing and the instantaneous value of the output voltage V30 at the second sampling timing. Accordingly, there occur no alarm failures and false alarms, which is advantageous, even if the operating point of the output voltage V30 fluctuates due to the influence of ambient light, such as ambient light from a fluorescent lamp or incandescent light, that strikes into the sensing space. In the present embodiment, thus, the presence or absence of smoke is determined on the basis of the amount of change of the output voltage V30 upon pulsed emission by the LED 6. As a result, it becomes possible to avoid alarm failures, in which fire is not determined to have occurred, despite reception, by the photodiode PD, of light from the LED 6, as well as false alarms, in which fire is determined to have occurred although the photodiode PD is not receiving light from the LED 6.

Figure 14:
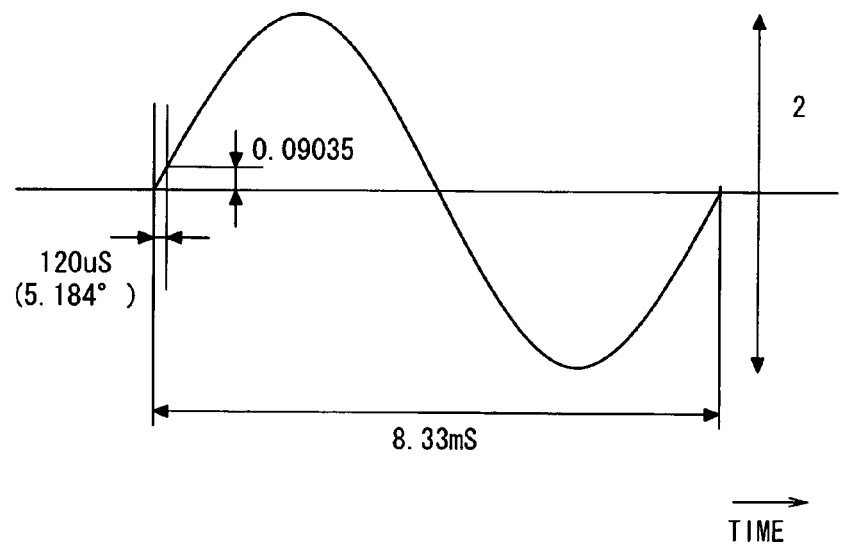
FIG. 14 is a waveform diagram illustrating the operation of Embodiment 6.

For instance, in a case where light from a fluorescent lamp that is lighted by a commercial power source (60 Hz AC power source) using a Cu—Fe-type ballast strikes into the sensing space, the output voltage V30 fluctuates sinusoidally at a frequency of 120 Hz, as illustrated in FIG. 14, due to the influence of light flicker from the fluorescent lamp. The fluctuation period of the output voltage V30 is 8.33 ms. Therefore, the maximum fluctuation amount of the output voltage V30 that can be generated due to the influence of the fluorescent lamp, in an interval of 120 μs, is worked out as follows, assuming a peak to peak amplitude of "2" for the output voltage V30. That is, the maximum fluctuation amount is "0.09035", since 360°×(120 μs/8.3 ms)=5.184°, and sin(5.184°=0.09035. This value (0.09035) is about 4.5% of the original amplitude (2) (0.09035/2=0.045175). Therefore, the fluctuation amount of the output voltage V30 due to the influence of the fluorescent lamp can be attenuated to about 4.5% (−26.9 dB) by setting the first sampling timing and second sampling timing to an interval of 120 μs.

As a result, alarm failures and false alarms are less likely to occur even when the operating point of the output voltage V30 fluctuates owing to a greater low-frequency component comprised in the input current I20 on account of increased amount of ambient light received by the photodiode PD. In consequence, the structure of the labyrinth can be greatly simplified, or the labyrinth itself may be omitted, which allows reducing the cost of the smoke sensor A.

Figure 15:
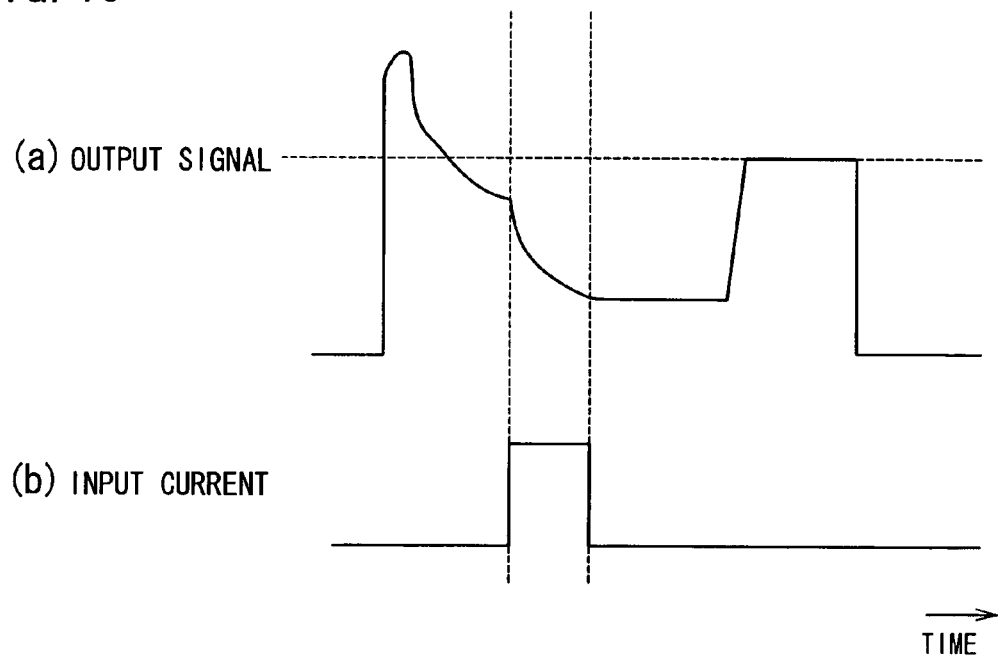
FIG. 15 is a time chart illustrating the operation of Embodiment 6.

In the present embodiment, the circuit block 30 is envisaged to be driven intermittently. Therefore, the output voltage V30 may exhibit comparatively large fluctuations, as illustrated in FIG. 15, immediately after startup of the sensor output processing section 31. Herein, occurrence of alarm failures and false alarms, due to the influence of the fluctuation of output voltage V30 immediately after startup of the sensor output processing section 31, can be avoided by determining the presence or absence of smoke on the basis of the amount of change of the output voltage V30 upon pulsed emission by the LED 6, as described above.

Figure 16:
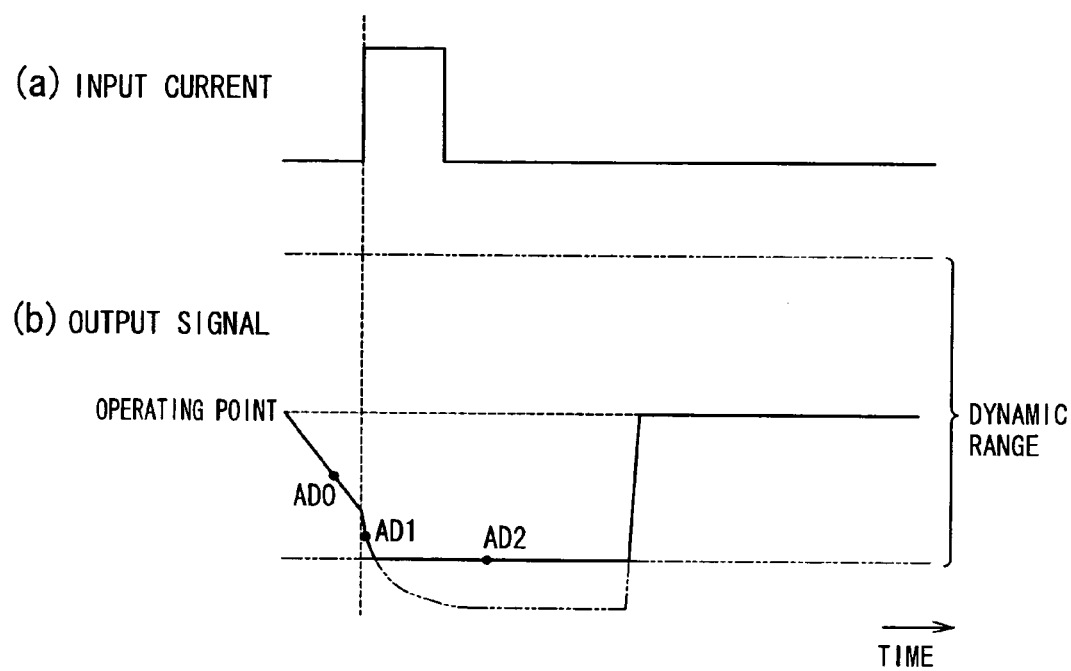
FIG. 16 is a time chart illustrating the operation of Embodiment 6.

The output voltage V30 may become saturated in some cases when the low-frequency component comprised in the input current I20 is equal to or greater than a certain magnitude, as illustrated in FIG. 16, due to the influence of ambient light. In particular, the output voltage V30 becomes saturated comparatively readily if a battery is used as the power source of the smoke sensor, as in the present embodiment, since in this case the power source voltage of the operational amplifiers is low and the dynamic range of the operational amplifiers comparatively narrow. If the input current I20 is increased, then the output voltage V30 cannot further track the fluctuation of the input current I20 if the output voltage V30 becomes saturated halfway through. As a result, there is a chance of alarm failure in that the amount of change of the output voltage V30 does not reach the fire determination level, even if the pulsed sensor current I10 is generated through reception, by the photodiode PD, of light from the LED 6 (the output voltage V30 in a non-saturated instance is denoted by a double dotted line in (b) of FIG. 16).

In the present embodiment, therefore, the instantaneous value of the output voltage V30 at a preliminary period before emission by the LED 6 is read as a preliminary value AD0, as illustrated in (b) of FIG. 16, so that if the preliminary value AD0 does not fall within a normal range established beforehand, determination by the determination circuit 38 is not carried out. This function is realized by preliminary determination means (not shown) provided in the operation processing section 32. Specifically, the preliminary determination means detects, as the preliminary value AD0, the amount of change of the output voltage V30 from the operating point, due to ambient light, before the output voltage V30 fluctuates through reception of the pulsed emission of the LED 6. If the amount of change exceeds a normal range, the preliminary determination means determines that there is a chance that the output voltage V30 is saturated, and prevents the determination circuit 38 from determining the presence or absence of smoke. This allows avoiding alarm failures that occur when the output voltage V30 becomes saturated due to ambient light, and the fluctuation amount of the output voltage V30, derived from the pulsed emission of the LED 6, fails to be detected accurately.

Embodiment 7

Figure 17:
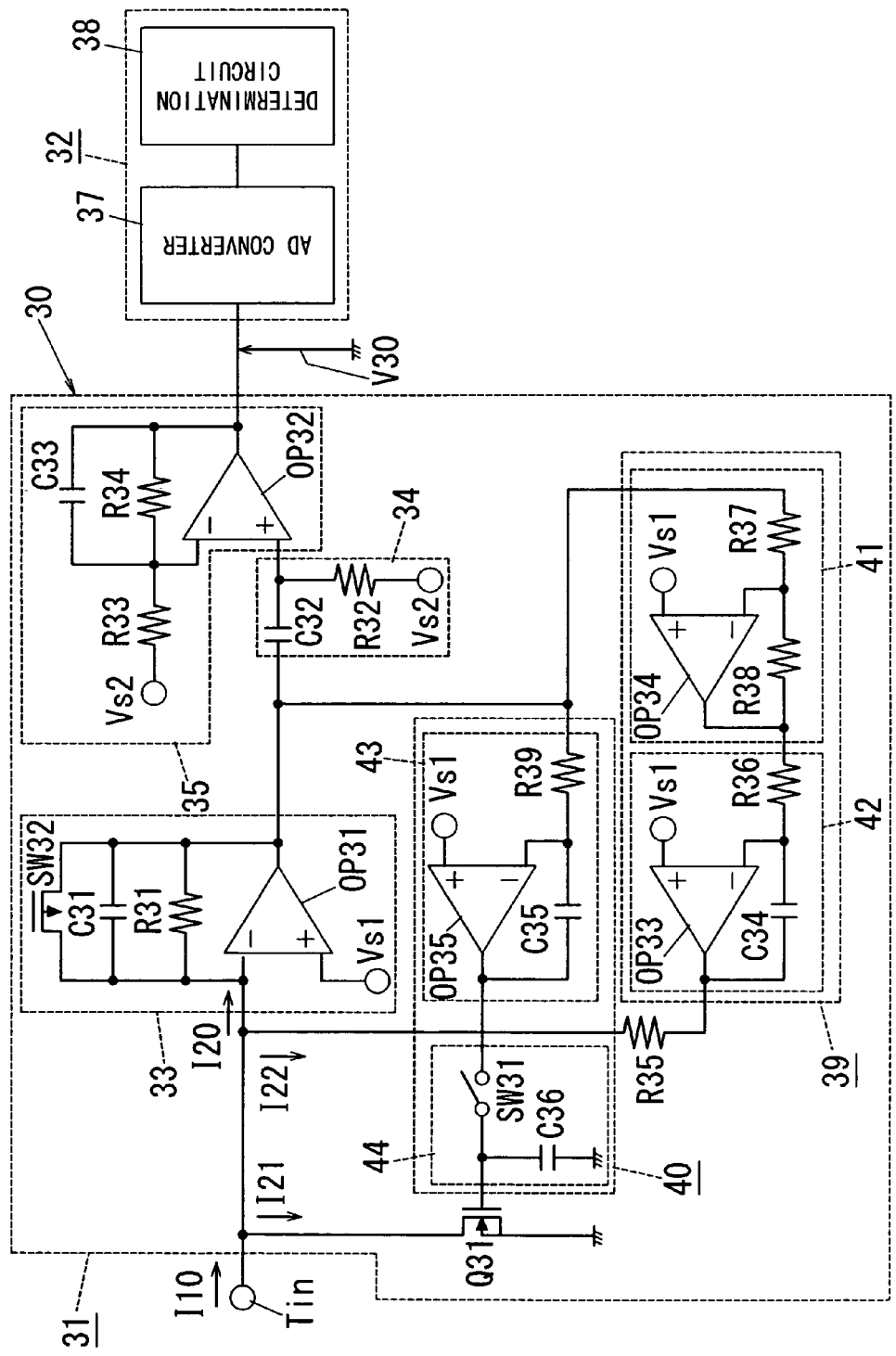
FIG. 17 is a schematic circuit diagram illustrating the configuration of Embodiment 7 of the present invention.

In the smoke sensor A of the present embodiment, the sensor output processing section 31 comprises a second feedback circuit 39 and a correcting resistor R35, as well as a first feedback circuit 40 and a correcting transistor Q31, as illustrated in FIG. 17. The second feedback circuit 39 outputs voltage according to the magnitude of a low-frequency component no greater than a predefined second cut-off frequency fc2, of the output voltage of the current-voltage conversion circuit 33. The correcting resistor R35 is inserted between the output of the second feedback circuit 39 and a connection terminal Tin of the current-voltage conversion circuit 33. The first feedback circuit 40 outputs voltage according to the magnitude of a low-frequency component no greater than a predefined first cut-off frequency fc1, of the output voltage of the current-voltage conversion circuit 33. The correcting transistor Q31 is configured in such a way so as extract, from the sensor current I10, current according to the magnitude of the output of the first feedback circuit 40.

The second feedback circuit 39 has an inverting amplifier circuit 41 and a second integrating circuit 42. The inverting amplifier circuit 41 inverts and amplifies the output voltage of the current-voltage conversion circuit 33. The second integrating circuit 42 integrates the output voltage inverted and amplified by the inverting amplifier circuit 41, and outputs an integration voltage corresponding to the integration value component of the output voltage.

The second integrating circuit 42 comprises an operational amplifier OP33, such that an inverting input terminal of the operational amplifier OP33 is connected to the output of the inverting amplifier circuit 41 via a resistor R36, and a capacitor C34 is connected between the output terminal and the inverting input terminal of the operational amplifier OP33. As a result, the second integrating circuit 42 functions as a low-pass filter having a time constant determined by the resistor R36 and the capacitor C34. The time constant of the integrating circuit 42 is set in such a manner that the integrating circuit 42 has a second cut-off frequency fc2 that blocks at least output voltage corresponding to a sensor current I10 (hereafter, detection signal) that is generated upon reception, by the photodiode PD, of light from the LED 6.

The inverting amplifier circuit 41 is provided in order to bring the output of the integrating circuit 42 in-phase with respect to the output voltage of the current-voltage conversion circuit 33. The inverting amplifier circuit 41 comprises an operational amplifier OP34, such that an inverting input terminal of the operational amplifier OP34 is connected to the output terminal of the current-voltage conversion circuit 33 via a resistor R37, and a resistor R38 is connected between the output terminal and the inverting input terminal of the operational amplifier OP34. The non-inverting input terminals of the two operational amplifiers OP33, OP34 are brought to the same potential as the reference voltage Vs1, with respect to ground.

In a case where the input current I20 of the current-voltage conversion circuit 33 comprises the detection signal and a low-frequency component, the integration voltage outputted by the second integrating circuit 42 is a voltage corresponding to the low-frequency component. In this case, the input current I20 is phase-reversed first in the current-voltage conversion circuit 33, and is further reversed once at each of the inverting amplifier circuit 41 and the integrating circuit 42. As a result, an integration voltage of opposite phase to the input current I20 appears in the output of the integrating circuit 42. Herein, the connection terminal Tin of the current-voltage conversion circuit 33 is at the same potential as the reference voltage Vs1, with respect to ground. Therefore, there arises a potential difference, in which the integration voltage is subtracted from the reference voltage Vs, between the two ends of the correcting resistor R35. As a result, the correction current I22 can be extracted from the sensor current I10 through causing the correction current I22, corresponding to the magnitude of the integration voltage, to flow through the correcting resistor R35. That is, in a case where a low-frequency component is comprised in the sensor current I10, the current from which the low-frequency component has been subtracted is inputted, as the input current I20, into the current-voltage conversion circuit 33, as a result of which the low-frequency component is removed from the output voltage.

In the circuit block 30 of the present embodiment, the first feedback circuit 40 has a first integrating circuit 43 and a sample-and-hold-circuit 44. The first integrating circuit 43 integrates the output voltage of the current-voltage conversion circuit 33, and the sample-and-hold-circuit 44 samples and holds the output of the first integrating circuit 43.

The first integrating circuit 43 comprises an operational amplifier OP35, such that an inverting input terminal of the operational amplifier OP35 is connected to an output terminal Tout of the current-voltage conversion circuit 33 via a resistor R39, and a capacitor C35 is connected between the output terminal and the inverting input terminal of the operational amplifier OP35. The first integrating circuit 43 functions as a low-pass filter having a time constant determined by the resistor R39 and the capacitor C35. The time constant is set in such a manner that the first integrating circuit 43 has a first cut-off frequency fc1 that is higher than the second cut-off frequency fc2 of the second integrating circuit 42 (i.e. fc2<fc1). The non-inverting input terminal of the operational amplifier OP35 is brought to the same potential as the reference voltage Vs1, with respect to ground.

A correcting transistor Q31 is inserted between the connection terminal Tin and ground (predefined potential point). Herein, the correcting transistor Q31 is configured as an N channel MOSFET in such a manner that the correction current I21 according to the output of the first integrating circuit 43 flows from the connection terminal Tin to ground. The drain of the correcting transistor Q31 is connected to the connection terminal Tin, the source is connected to ground, and the gate is connected to the output of the first integrating circuit 43 (output terminal of the operational amplifier OP35), via the sample-and-hold-circuit 44.

The sample-and-hold-circuit 44 has a capacitor C36 and a normally-closed first switch SW31. The first switch SW31 is inserted between the output of the first integrating circuit 43 and the gate of the correcting transistor Q31. The capacitor C36 is connected between the gate of the correcting transistor Q31 and ground. The sample-and-hold-circuit 44 switches off the first switch SW31 at a predefined timing, whereby the output of the integrating circuit 43 is sustained, as the output voltage of the capacitor C36, for the above predefined timing.

Thanks to the above-described configuration, the low-frequency component no greater than the first cut-off frequency fc1, of the output voltage, appears in the output of the first integrating circuit 43, through integration, by the first integrating circuit 43, of the output voltage of the current-voltage conversion circuit 33. In this case, the input current I20 is phase-reversed first in the current-voltage conversion circuit 33, and is further reversed in the first integrating circuit 43. As a result, there appears a low-frequency component, in-phase with the input current I20, in the output of the integrating circuit 43. The output of the integrating circuit 43 is applied to the gate of the correcting transistor Q31 via the sample-and-hold-circuit 44. As a result, a current according to the magnitude of the output of the integrating circuit 43 flows between the drain and source of the correcting transistor Q31, with the switch SW31 of the sample-and-hold-circuit 44 in an on-state. Therefore, a low-frequency component no greater than the first cut-off frequency fc1 and comprised in the sensor current I10 can be extracted to the correcting transistor Q31, and the gain of the low-frequency component can be reduced in the sensor output processing section 31 as a whole.

When the switch SW31 of the sample-and-hold-circuit 44 is switched off, the output of the integrating circuit 43 is cut off from the gate of the correcting transistor Q31. However, the output of the integrating circuit 43 is sustained as the two-terminal voltage of the capacitor C36. As a result, the correction current I21, according to the magnitude of the output of the integrating circuit 43 immediately before switching-off of the switch SW31, can be caused to continue flowing between the drain and source of the correcting transistor Q31. In other words, when the sample-and-hold-circuit 44 operates, through switching-off of the switch SW31 of the sample-and-hold-circuit 44, there drops the upper limit value (first cut-off frequency fc1) of the frequency of the correction current I21 that can flow between the drain and the source of the correcting transistor Q31. The DC component can be removed from the output voltage by being extracted next to the correcting transistor Q31.

In the present embodiment, the timing at which the switch SW31 of the sample-and-hold-circuit 44 is switched off is set in accordance with the period at which the LED 6 of the smoke sensor outputs pulsed light, i.e. the period at which there is detected the presence or absence of smoke flowing into the sensing space (hereafter, sensing period). In the sensor output processing section 31 of the present embodiment, thus, a detection signal generated when the photodiode PD receives light from the LED 6, during the above-mentioned sensing period, is converted into voltage, and is outputted as the output voltage V30. Therefore, the switch SW31 is off at the sensing period, in such a manner so as to preclude the detection signal from being extracted to the correcting transistor Q31 during the sensing period.

In a more detailed explanation, the first cut-off frequency fc1 of the first integrating circuit 43 is set to be closer to the frequency of the detection signal than to the second cut-off frequency fc2 of the second integrating circuit 42. As a result, it is possible that, with the switch SW31 in an on state, the detection signal is extracted to the correcting transistor Q31 and that there decreases the gain of the detection signal in the sensor output processing section 31 as a whole. In the present embodiment, therefore, the sample-and-hold-circuit 44 is operated through switching-off of the switch SW31 in the sensing period, whereby the detection signal is prevented from being extracted to the correcting transistor Q1, and the gain of the detection signal is kept high in the sensor output processing section 31 as a whole.

In the sensing period at which the switch SW31 is switched off, the output of the first feedback circuit 40 is fixed to the value immediately before the switch SW31 is switched off.

Therefore, the fluctuation-free DC component comprised in the sensor current I10 can be continuously extracted to the correcting transistor Q31. Meanwhile, the low-frequency component having fluctuation and comprised in the sensor current I10 cannot be extracted to the correcting transistor Q31, even if the low-frequency component is no greater than the first cut-off frequency fc1.

In the sensing period, however, the low-frequency component no greater than the second cut-off frequency fc2 can be extracted to the correcting resistor R35 by being removed as the output of the second feedback circuit 39.

In the circuit block 30 having the above-described configuration, it becomes thus possible to extract a greater current component, as compared with a case where the low-frequency component is extracted only by the correcting resistor R35, through the use of the correcting transistor Q31 and the correcting resistor R35 as means for extracting the low-frequency component of the sensor current I10.

In the example of FIG. 17, there is provided a second switch SW32 connected in parallel to the converting resistor R31 of the current-voltage conversion circuit 33. The switch SW32 is a normally-closed switch that is switched off at the same timing as the first switch SW31 and that has the below-described function.

If, hypothetically, only the first switch SW31 is provided, then the cut-off frequency fc1 of the first feedback circuit 40 shifts to a high frequency-side when the first switch SW31 is switched on. As a result, there collapses the gain on the low-frequency side, in the gain frequency characteristic of the sensor output processing section 31 as a whole, when the first switch SW31 is switched on. A gain peak appears as a result between the cut-off frequency fc0 and the first cut-off frequency fc1, and system oscillation becomes likelier, i.e. the output voltage V30 is likelier to oscillate. This is problematic in that, as a result, the rise in the output voltage V30 becomes delayed when the first switch SW31 is switched off at a time where the output voltage V30 is low.

In the present embodiment, by contrast, the second switch SW32 is connected in parallel to the converting resistor R31. As a result, the gain of the sensor output processing section 31 collapses through connection between both ends of the converting resistor R31, during the time at which the first switch SW31 is switched on, trough switching-on of the second switch SW32, together with the first switch SW31. This allows canceling the above-described gain peak, which in turn allows suppressing system oscillation caused by switching-on of the first switch SW31.

Figure 18A:
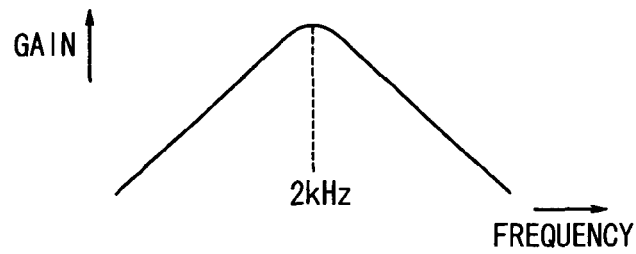
FIG. 18(a) is a characteristic diagram illustrating the gain in a sensor output processing section of Embodiment 7.
Figure 18B:
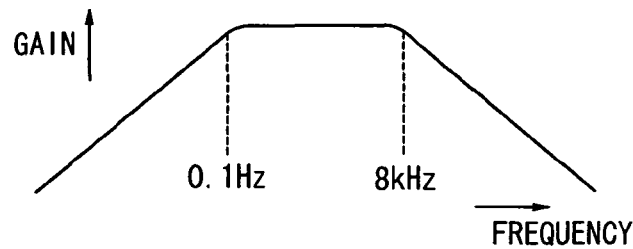
FIG. 18(b) is a characteristic diagram illustrating the gain in a sensor output processing section of Embodiment 6.

In the present embodiment, a predefined frequency (herein, 2 kHz), as illustrated in FIG. 18(a), is used as the reference frequency for the gain frequency characteristic in the sensor output processing section 31. A gain peak arises at the reference frequency by depressing the gain at higher and lower frequencies than the reference frequency. In the present embodiment, thus, gain is imparted to a comparatively narrow frequency band around the reference frequency. In Embodiment 6, by contrast, as illustrated in FIG. 18(b), there was set a gain frequency characteristic of the sensor output processing section 31 in such a manner that the gain was flat over a comparatively wide frequency band (herein, from 0.1 Hz to 8 kHz).

Specifically, the time constant of the high-pass filter 34 is adjusted to cause thereby the high-pass filter 34 to function as a differentiating circuit. As a result, the signal integrated by the integrating circuit (resistor R31 and capacitor C31) provided in the current-voltage conversion circuit 33 is differentiated at the subsequent high-pass filter 34. In short, the low-pass filter function of the current-voltage conversion circuit 33, which is the integrating circuit, and the high-pass filter 34, as the differentiating circuit, function both as band pass means that generates a gain peak at a predefined frequency band (frequency band centered around a reference frequency).

The above-described reference frequency is decided in accordance with pulse width upon pulsed emission by the LED 6, in such a manner that the amplitude of the output voltage V30 with respect to the input current I20 is maximum. For instance, the reference frequency is preferably set to 2 kHz in a case where the pulse width of the pulsed emission is 90 μs. It becomes thus possible to increase the amplitude of the output voltage V30 with respect to the input current I20 by imparting gain to a narrow frequency band centered around a reference frequency that is determined in accordance with pulse width of the input current I20.

Figure 19:
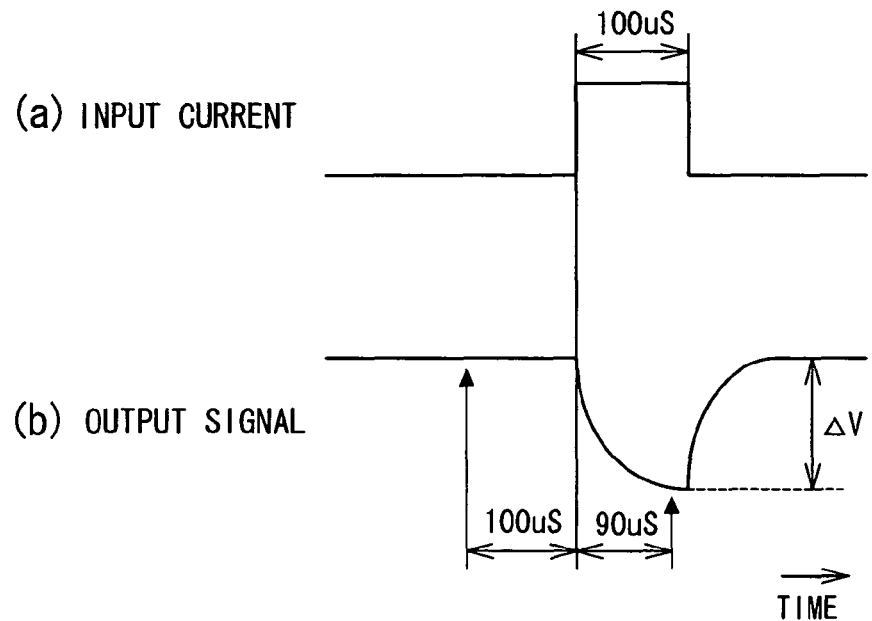
FIG. 19 is a time chart illustrating the operation of Embodiment 6.

In the configuration of Embodiment 6, the output voltage V30 starts dropping from the operating point in concert with the rise of the input current I20, as illustrated in (b) of FIG. 19, when the pulsed input current I20 flows, as illustrated in (a) of FIG. 19 upon reception, by the photodiode PD, of light from the LED 6. Thereafter, the output voltage V30 starts rising towards the operating point in concert with the drop of the input current I20. Thus, the output voltage oscillates only to one side of the operating point (herein, the smaller voltage side).

Figure 20:
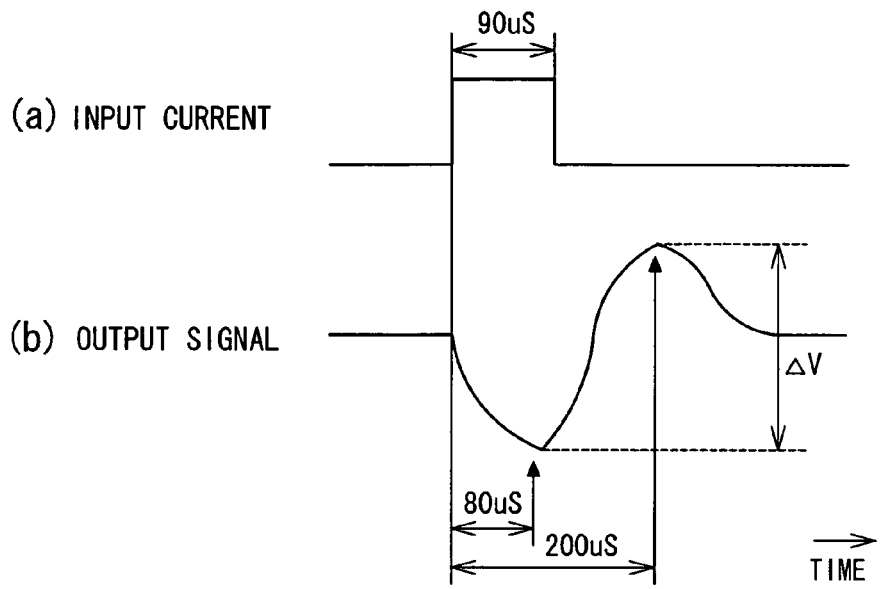
FIG. 20 is a time chart illustrating the operation of Embodiment 7.

In the present embodiment, by contrast, the output voltage V30 starts dropping from the operating point in concert with the rise of the input current I20, as illustrated in (b) of FIG. 20, when the pulsed input current I20 flows, as illustrated in (a) of FIG. 20 upon reception, by the photodiode PD, of light from the LED 6. The output voltage V30 starts rising then in concert with the drop of the input current I20. Thereafter, the output voltage V30 reaches a peak beyond the operating point, and starts dropping then towards the operating point. That is, the pulse signal integrated by the integrating circuit of the current-voltage conversion circuit 33 is differentiated by the subsequent high-pass filter 34, as a result of which the output voltage V30 oscillates on both sides of the operating point. The output voltage V30 oscillates thus on both sides of the operating point.

Accordingly, the present embodiment allows increasing the difference (ΔV) between the first and second measurement values, as compared with the case in the configuration of Embodiment 6, through sampling, for instance, each of upper and lower peaks of the output voltage V30. The SN ratio increases thereby, which is advantageous. In a case where the output voltage V30 oscillates only on one side of the operating point, as in Embodiment 6, the difference between the first and second measurement values can be used only as the difference with the operating points of the output voltage V30. By contrast, in a case where the output voltage V30 oscillates on both sides of the operating point, as in the present embodiment, the difference between the first and second measurement values can be used as a magnitude that is about twice that from the operating point to one of the peaks. The signal component removed from the output voltage V30 increases as a result, as does the SN ratio.

In a specific configuration, a gain peak for a reference frequency of 2 kHz arises, as illustrated in FIG. 18(a), under the following settings: converting resistor R31=5 MΩ, capacitor C31=14 pF, resistor R32=2 MΩ, capacitor C32=50 pF, resistor R33=39 kΩ, resistor R34=740 kΩ, capacitor C33=30 pF, correcting resistor R35=400 kΩ, resistor R36=500 kΩ, capacitor C34=200 pF, resistor R37=500 kΩ, resistor R38=40 kΩ, resistor R39=250 kΩ, capacitor C35=30 pF and capacitor C36=60 pF.

In the configuration of the present embodiment, sampling and holding need not be performed in order to detect the second measurement value, as is the case in Embodiment 6. Therefore, no sample-and-hold-circuit 36 is required in the operation processing section 32, which is advantageous.

From the viewpoint of increasing the difference between the first and second measurement values, however, it is preferably to respectively set the first sampling timing and second sampling timing in the vicinity of a peak (lower limit value and upper limit value) of the output voltage V30. However, the magnitude of the peak depends on the gain frequency characteristic of the sensor output processing section 31. Therefore, in some cases the peak of the output voltage V30 also changes when there varies the gain frequency characteristic of the sensor output processing section 31 depending on, for instance, the temperature characteristic of the constituent components of the sensor output processing section 31. Changes in the peak of the output voltage V30 obviously entail changes in the magnitude of the difference between the first and second measurement values. In the present embodiment, therefore, the first sampling timing and second sampling timing are set to be ahead of a peak of the output voltage V30 in the time axis direction. As a result, variability in the difference between the first and second measurement values, caused by variability of the gain frequency characteristic of the sensor output processing section 31, can be kept as small as possible.

Figure 21:
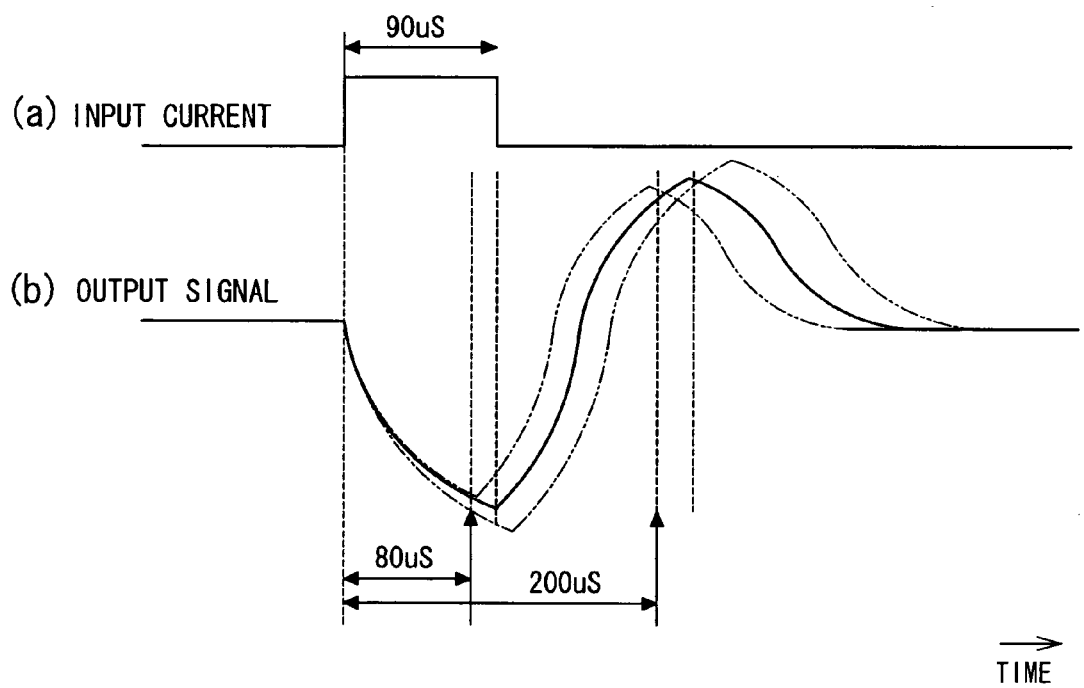
FIG. 21 is a time chart illustrating the operation of Embodiment 7.

As illustrated in FIG. 21, specifically, the first sampling timing and second sampling timing are set to be ahead of the peak of the output voltage V30 at a time when the gain frequency characteristic of the sensor output processing section 31 is in a steady state. As a result, the variability of the measurement values, due to gain variability of the sensor output processing section 31, can be kept smaller than in a case where the first sampling timing and second sampling timing are set to a peak of output voltage V30 in the steady state. The extent of shift of the first sampling timing and second sampling timing, from the peak of output voltage V30, in the steady state, is decided in such a manner that the variability of the respective measurement values lies within a prescribed target precision range. In the example of the figure, the pulse width of the pulsed emission by the LED 6 is set to 90 µs, and the first sampling timing and second sampling timing are respectively set to 80 µs and 200 µs from emission start.

Figure 22:
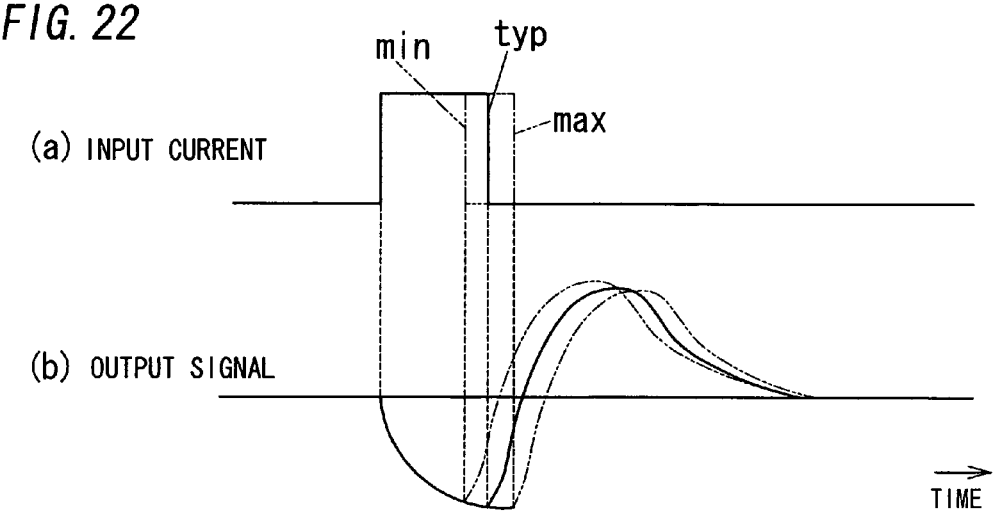
FIG. 22 is a time chart illustrating the operation of Embodiment 7.

As illustrated in (a) of FIG. 22 (in the figure, the steady state is denoted as "typ", the maximum value as "max" and the minimum value as "min") the pulse width of the input current I20 may sometimes vary within a given range, on account of, for instance, the temperature characteristic of the LED driving circuit 18 (see FIGS. 30(a) and 30(b)). The peak position of the output voltage V30 in the time axis direction varies also, as indicated by the double-dotted line of (b) of FIG. 22, in response to changes in the pulse width of the input current I20. Accordingly, the first and second measurement values exhibit variability even if the sampling timing is set fixedly. In the present embodiment, thus, the same clock in the LED driving circuit 18 that defines the pulse width of the input current I20 is shared as the clock for deciding the sampling timing.

As a result, the sampling timing is decided in accordance with pulse width after changes in the pulse width of the input current I20 that occur on account of, for instance, the temperature characteristic of the LED driving circuit 18. The variability of the first and second measurement values, which arises from variability in the pulse width of the input current I20, can be suppressed as a result.

The above embodiments have been explained assuming a configuration wherein the sensor current I10 flows from the photodiode PD to the connection terminal Tin, when the photodiode PD receives light. The embodiments, however, are not limited to that configuration, which may also be one wherein the orientation of the sensor current I10 with respect to the connection terminal Tin is reversed, so that the sensor current I10 flows from the connection terminal Tin to the photodiode PD when the photodiode PD receives light. In this case, the sensor output processing section 31 functions as a current source that supplies the sensor current I10 to the photodiode PD. Specifically, the current-voltage conversion circuit 2 is configured in such a manner that the correcting transistor Q31 comprises, in this case, a P channel MOSFET connected between the connection terminal Tin and a predefined potential point, and current according to the output of the first integrating circuit 43 flows from the predefined potential point to the connection terminal Tin. As a result, the correcting resistor R5 and the correcting transistor Q1 do not function so as to extract the correction currents I21, I22 from the photodiode PD, but function so as to supply the correction currents I21, I22 to the photodiode PD.

Other features and functions are identical to those of Embodiment 6.

Embodiment 8

A smoke sensor A of the present embodiment has a sensing space in a housing 20. Further, the smoke sensor A comprises an LED (light-emitting section) 6, a photodiode (light-receiving section) PD and a circuit block 50. The LED 6 intermittently outputs pulsed light towards the sensing space. The photodiode PD is disposed at a position at which direct light from the LED 6 is not incident, and converts received light into current. The circuit block 50 is configured in such a manner so as to detect smoke in the sensing space, on the basis of an input current from the photodiode PD. When smoke flows into the sensing space in the smoke sensor A, the light from the LED 6 is diffused and reflected by the smoke in the sensing space, as a result of which there increases the amount of light from the LED 6 received at the photodiode PD, and there increases the amount of current outputted by the photodiode PD. In the smoke sensor A exemplified herein, a battery is used as a power source. Driving is performed intermittently in order to curb average power consumption and to prolong battery life.

Figure 23:
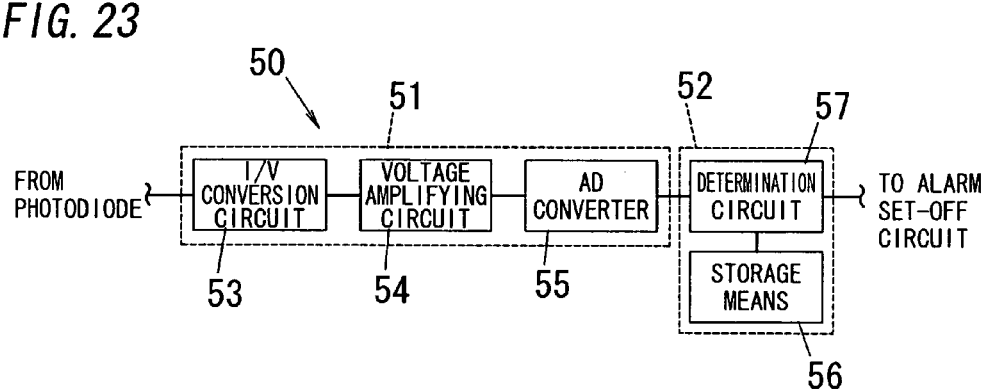
FIG. 23 is a schematic block diagram illustrating the configuration of Embodiment 8 of the present invention.

A circuit block 50 of the present embodiment comprises a detection processing section 51 and a determination processing section 52, as illustrated in FIG. 23. The detection processing section 51 obtains a detection value corresponding to the smoke concentration in the sensing space, on the basis of an input current inputted by the photodiode PD. The determination processing section 52 is provided after the detection processing section 51, and determines the presence or absence of fire on the basis of the detection value.

As illustrated in FIG. 23, the detection processing section 51 comprises a current-voltage conversion circuit (I/V conversion circuit) 53 that converts an input current, inputted through an input terminal, to an output voltage whose voltage value fluctuates according to the fluctuation of the input current, and that outputs the output voltage. Further, the detection processing section 51 comprises a voltage amplifying circuit 54 connected to the output of the current-voltage conversion circuit 53 and that amplifies the output voltage, and an AD converter 55 that converts the output (hereafter, output voltage) of the voltage amplifying circuit 54 to a digital value. The AD converter 55 samples and quantizes the output voltage, to extract thereby, in the form of a digital value, a fluctuation component (detection value) of the output voltage that arises through reception, by the photodiode PD, of light from the LED 6. With the input current from the photodiode PD in a zero state, the detection processing section 51 in the above configuration uses, as an operating point, an instantaneous value of the output voltage, and outputs, as a detection value, the amount of change, from the operating point, of the output voltage according to the fluctuation of the input current, to the subsequent determination processing section 52.

The determination processing section 52 has storage means 56 that stores a below-described determination level. The determination processing section 52 further has a determination circuit 57, as determination means that detects the presence or absence of smoke in the sensing space on the basis of the output (detection value) of the AD converter 55. The determination circuit 57 determines the presence or absence of smoke in the sensing chamber by comparing the detection value with a predefined determination level in the storage means 56.

Figure 24:
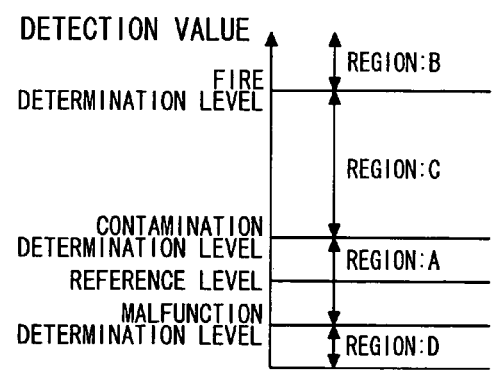
FIG. 24 is an explanatory diagram illustrating determination levels used in Embodiment 8.

As illustrated in FIG. 24, the determination level stored in the storage means 56 includes a reference level (corresponding to a detection value in a state where no smoke is in the sensing space), established beforehand, and a fire determination level, set higher than the reference level, as a fire criterion. The determination level includes a state determination level, set lower than the fire determination level, and that is used as a criterion for a predefined operating state other than fire. The determination circuit 57 determines simultaneously both the operating state and the presence or absence of fire by comparing a magnitude relationship between the detection value and each determination level.

Figure 25:
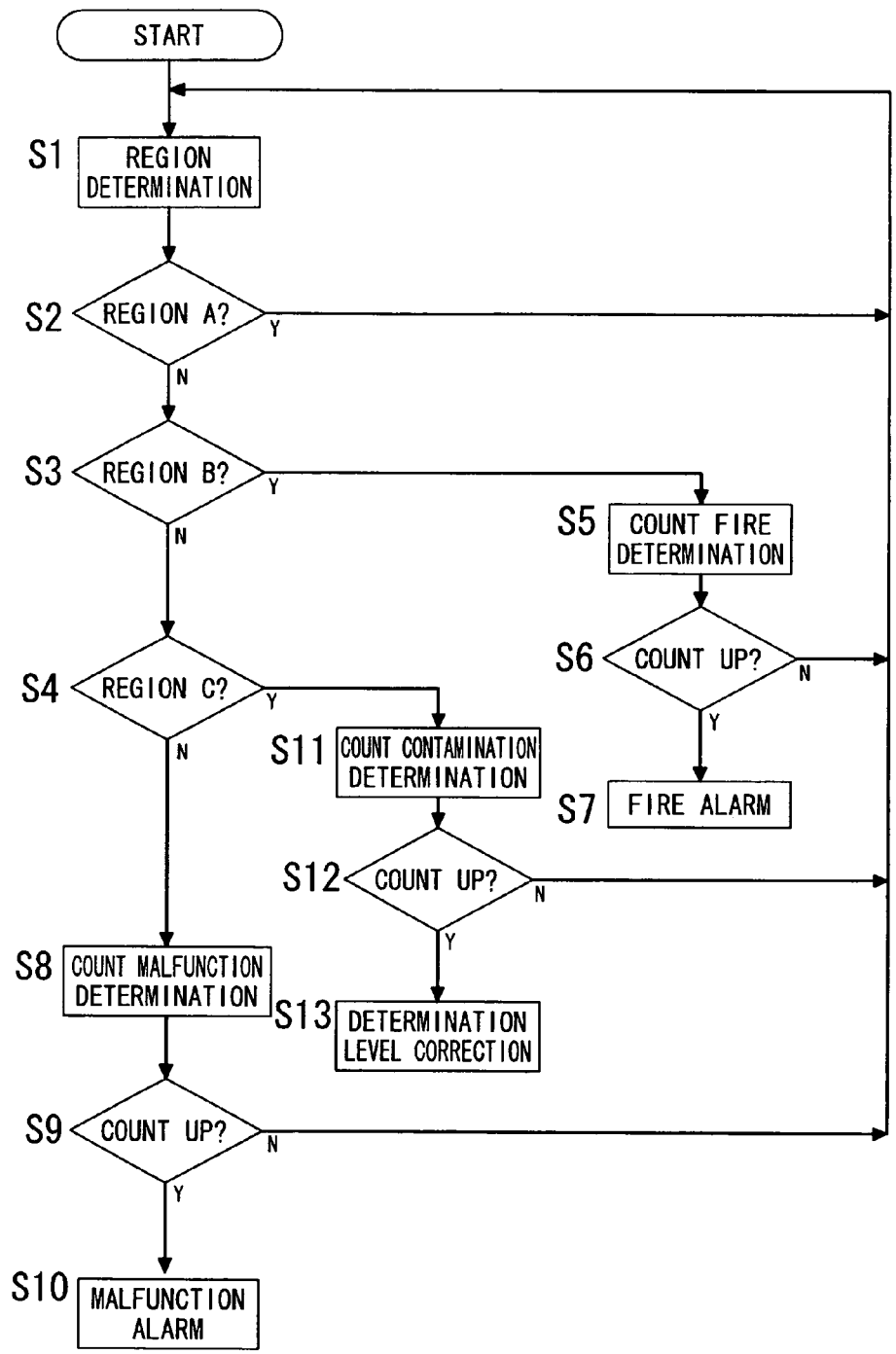
FIG. 25 is a flow chart illustrating the operation of Embodiment 8.

In the present embodiment, the state determination level includes a contamination determination level, set higher than the reference level, and that is a criterion for determining, as an operating state, the presence or absence of contamination in the sensing space. Specifically, the determination circuit 57 determines a region under which the detection value falls, by comparing the detection value with each determination level, as illustrated in FIG. 25 (S1). When the detection value falls under region B (see FIG. 24) of being equal to or greater than the fire determination level (S3: Yes), the determination circuit 57 determines that there is smoke in the sensing space (smoke concentration is reached that can be considered as that of a fire). When the detection value falls under region C (see FIG. 24) of being equal to or greater than the contamination determination level but smaller than the fire determination level (S4: Yes), the determination circuit 57 determines that there is contamination in the sensing space.

In the present embodiment, the state determination level further comprises a malfunction determination level set lower than the reference level and that is a criterion for determining malfunction of the smoke sensor A, as an operating state. When the detection value falls under region A (see FIG. 24) of being equal to or greater than the malfunction determination level but smaller than the contamination determination level (S2: Yes), the determination circuit 57 determines that the state is normal. When the detection value falls under region D (FIG. 24) of being smaller than the malfunction determination level (S4: No), the determination circuit 57 determines that malfunction has occurred. As a result, a malfunction can be determined to have occurred when the detection value lies outside a normal range, due to, for instance, abnormalities in an optical system.

Alarms or the like are not set off on the basis of a single determination by the determination circuit 57. Instead, the determination circuit 57 operates various counters for regions A to D under which the detection value falls, such that an alarm or the like is set off at a point in time at which the count value reaches a prescribed value.

In a concrete explanation, the determination circuit 57 operates a counter for fire determination whenever the determination circuit 57 determines that the detection value falls under region B (S5). When the count value reaches a prescribed value (S6: Yes), the determination circuit 57 confirms the determination to the effect that there is smoke, and initiates fire alarm set-off (S7). If the detection value falls under region D, the determination circuit 57 operates a counter for malfunction determination whenever the determination circuit 57 determines that the detection value falls under region D (S8). If the count value reaches a prescribed value (S9: Yes), the determination circuit 57 confirms the determination to the effect of malfunction, and initiates malfunction alarm set-off (S10).

If the detection value falls under region C, the determination circuit 57 operates a counter for contamination determination whenever the determination circuit 57 determines that the detection value falls under region C (S11). When the count value reaches a prescribed value (S12: Yes), the determination circuit 57 confirms the determination to the effect that there is contamination, and the fire determination level in the storage means 56 is corrected to a higher level (S13). In the smoke sensor A, the light from LED 6 is diffused and reflected not only by smoke flowing into the sensing space, but also by contamination, such as dust or the like, that is deposited on the inner peripheral surface of the sensing space, and is received by the photodiode PD. The detection value becomes greater in such cases as well, and hence the fire determination level is corrected by being hiked when it is determined that contamination is adhered in the sensing space, in such a way so as preclude false alarms caused by increases in the detection value due to contamination. The correction amount (hike amount) of the fire determination level is decided herein in accordance with the overamount of the detection value with respect to the contamination determination level (difference between the detection value and the contamination determination level).

The comparison between the detection value and each determination level (S1) is performed by the determination circuit 57 within a predefined period (for instance, a 8-second period). Since contamination does not become adhered quickly in the sensing space, however, the determination of whether the detection value falls under region C or not is performed once every correction period (for instance, one hour) established beforehand. At a timing other than the correction period, the counter for contamination determination is not operated, and the state is determined to be normal, even if it is determined that the detection value falls under region C. Moreover, the count value in the counter for contamination determination is reduced, through down counting, if the detection value falls outside region C during the correction period. The determination circuit 57 checks for the presence or absence of contamination (i.e. whether the detection value falls under region C) at each correction period. If the determination circuit 57 determines that there is contamination (i.e. that the detection value falls under region C) with a frequency equal to or greater than a prescribed value (for instance, eight times out of ten), the fire determination level in the storage means 56 is corrected to a higher level.

When in the present embodiment the determination circuit 57 determines that smoke is present, the time that elapses since smoke flows into the sensing space up to fire alarm set-off is shortened by making the period at which each determination level and the detection value are compared by the determination circuit 57 (hereafter, determination period) shorter than the determination period in the steady state. That is, the determination period is modified to a shorter one (for instance, from a 8-second period to a 4-second period) upon start of the operation of the counter for fire determination when the detection value falls under region B.

In a specific example, there may be used, as the counter for fire determination, a counter capable of counting from 0 to 5, such that the determination period is shortened then when the detection value falls under region B, whereby the count value changes from "0" to "1". In this case, fire alarm set-off starts when the detection value falls under region B during the next determination, whereby the count value changes from "1" to "2", and when the detection value falls under region B in the next determination, whereby the count value changes from "2" to "3". Thereafter, the count value "3" is maintained for the time during which the detection value falls under region B, and is sequentially changed to "4", "5" and "0", at each determination, if the detection value falls outside region B. Fire alarm set-off continues while the count value is "4" or "5". When the count value reverts to "0", fire alarm set-off is terminated and the determination period is restored to the original determination period (for instance, is modified from a 4-second period to an 8-second period).

The determination circuit 57 functions also as level calculation means that calculates a state determination level using at least one from among the reference level and the fire determination level (contamination determination level and malfunction determination level), and that stores the calculated state determination level in the storage means 56. Specifically, only the reference level and the fire determination level are set beforehand, for instance before factory shipping, as determination levels, and the state determination level (contamination determination level and malfunction determination level) is calculated automatically by the determination circuit 57.

Herein, the contamination determination level is assumed to be defined as $(ADF-AD0)/4+AD0$, wherein $AD0$ is the reference level and $ADF$ is the fire determination level, and the malfunction determination level is assumed to be defined as $(AD0)/2$. This way, the fire determination level and the malfunction determination level need not be set separately, and thus the setting of the determination level can be made less burdensome, which is advantageous. In case that the contamination determination level is calculated using the fire determination level, as described above, the contamination determination level is corrected also accompanying the correction of the fire determination level, upon confirmation of the determination to the effect that there is contamination. This makes it unnecessary to correct the contamination determination level when the sensing space is contaminated, which is advantageous. That is, the contamination determination level calculated on the basis of the fire determination level is corrected automatically when the fire determination level is hiked upon confirmation of the determination to the effect that there is contamination. Also, the contamination determination level and the malfunction determination level can be set comparatively flexibly, in terms of, for instance, modifying the contamination determination level and the malfunction determination level in accordance with the installation environment of the smoke sensor A.

The definitions of the contamination determination level and the malfunction determination level are not limited to the above-described examples. Ordinarily, the magnitude of the detection value exhibits a variability of about 10% arising from, for instance, the temperature characteristic of circuit constituent components. Therefore, the malfunction determination level is preferably no greater than 80% of the reference level, so as to prevent determination of malfunction occurrence due to the influence of the above variability.

The determination result by the determination circuit 57 is sent to an alarm set-off circuit (not shown), and is notified by an appropriate method upon occurrence of fire (i.e. upon determination that there is smoke), or upon malfunction determination (i.e. upon determination of malfunction occurrence). The smoke sensor A may also be configured in such a manner that the above determination result is sent to an external device such as a home information panel or the like.

In the above-described configuration, both a process of determining the presence or absence of smoke in the sensing space and a process of determining the operating state are performed, once each, by the determination circuit 57, by comparing the detection value and the plurality of determination levels stored in the storage means 56. As a result, processing time can be shortened vis-à-vis conventional cases in which the process for fire determination and the process of determining the operating state (presence or absence of contamination in the sensing space and presence or absence of malfunction) are carried out separately. In the determination circuit 57, moreover, the fire determination level is corrected to a higher level if, upon checking of the presence or absence of contamination for each predefined correction period, it is determined that there is contamination with a frequency equal to or greater than a prescribed value. As a result, the correction frequency can be lowered, and the number of computation processes associated to the correction can be made fewer as compared with a conventional configuration in which the contamination state level must be subtracted from the detection value at every determination of the presence or absence of smoke. It becomes possible as a result to reduce the number of processes required for determining the presence or absence of smoke in the sensing space, vis-à-vis conventional cases, while preventing the occurrence of false alarms due to contamination in the sensing space.

Conventional smoke sensors included configurations in which separate circuits were used for various respective determinations (malfunction determination, contamination determination and so forth) other than fire determination. The circuit configuration in the present embodiment, by contrast, is simpler than such conventional configurations. This results in a smaller smoke sensor A having less power consumption, which is advantageous.

Determination of contamination in the sensing space (i.e. determination whether the detection value falls or not under region C) is not limited to being performed at each correction period established beforehand, as described above. For instance, contamination may be determined at an appropriate timing, for instance upon periodic inspection of the smoke detector A, so that the fire determination level in the storage means 56 is corrected to a higher level if contamination is determined to be present with a frequency equal to or greater than a prescribed value.

Embodiment 9

In the present embodiment there is explained the structure of a smoke sensor that uses a circuit block having the configuration explained in the above embodiments.

Figure 26A:
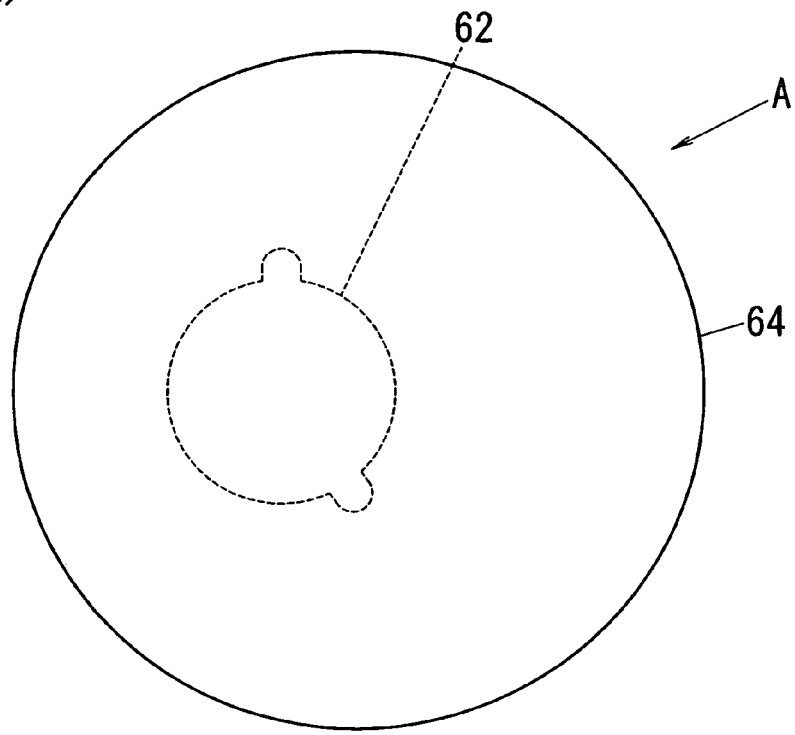
Figure 26B:
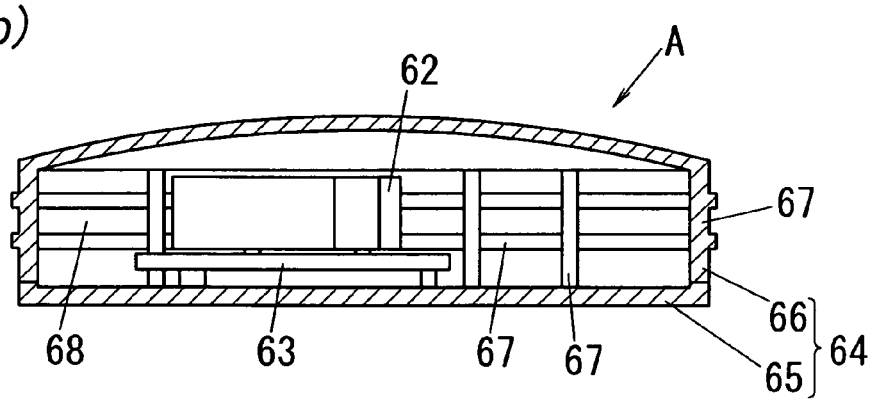

The smoke sensor of the present embodiment is attached to a ceiling or the like, and comprises a smoke detection body 62 in which an insect screen 60, provided with multiple air holes, covers a smoke detection chamber 61; a circuit board 63; and a disc-like body 64, as illustrated in FIGS. 26(a) and 26(b). A light-projecting element, a light-receiving element and other electronic components (not shown) are mounted on the circuit board 63. The body 64 accommodates the entire smoke detection body 62 and the circuit board 63, and hence the body 64 can exhibit an outer appearance having few irregularities. In FIG. 26(*b*), the smoke sensor A is depicted downside up, i.e. reversed with respect to the way it is attached to the ceiling surface.

The body 64 comprises a base 65 and a cover 66. Multiple openings 68 are formed, by criss-crossing bars 67, in the outer peripheral portion of the cover 66. Inside the body 64, the smoke detection body 62 is assembled integrally with the circuit board 63. The smoke detection body 62 may be provided on the top face (side of the ceiling face) or on the lower face of the circuit board 63.

Figure 27:
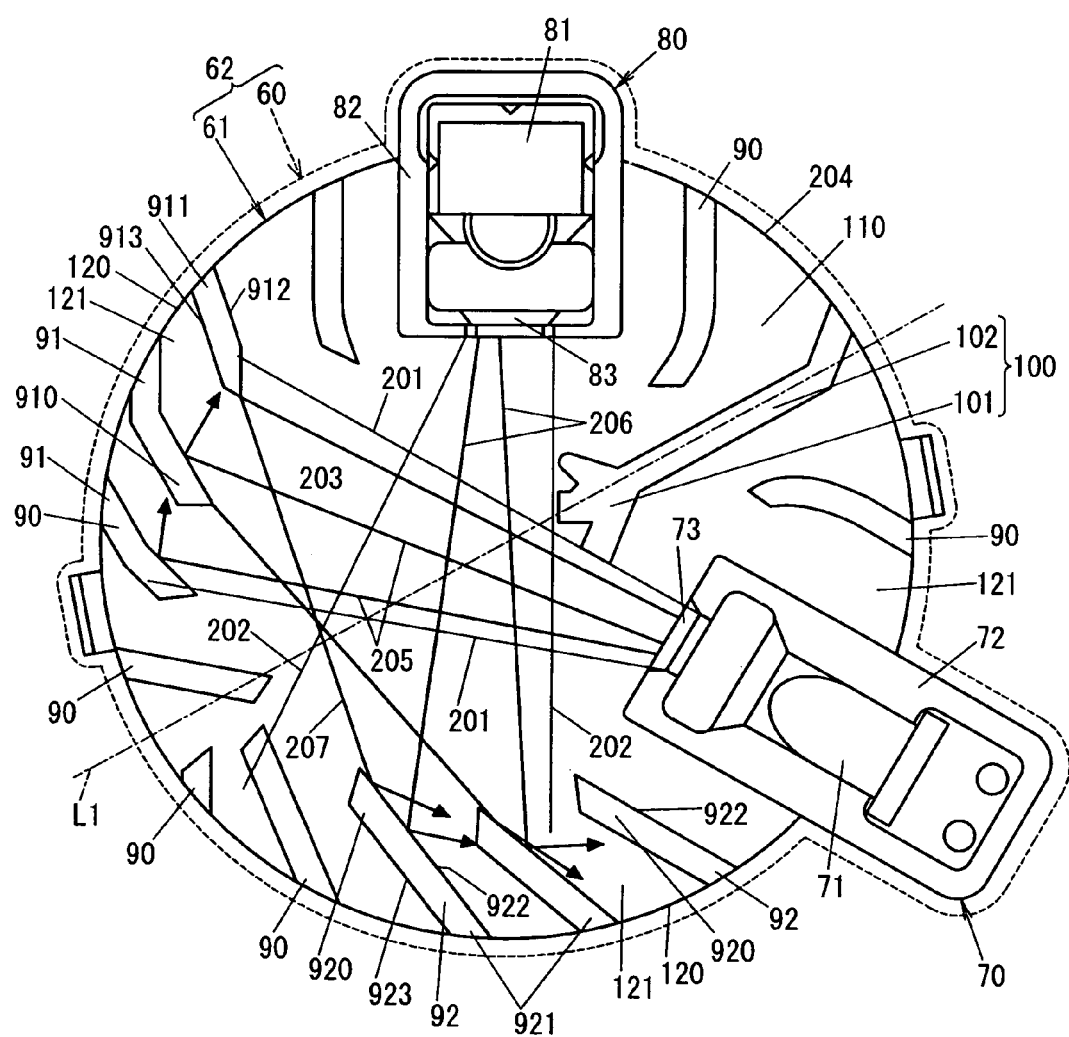
FIG. 27 is a schematic plan-view diagram illustrating the internal structure of a smoke detection chamber in Embodiment 9.

The inner structure of the smoke detection chamber 61 is explained below with reference to FIG. 27. In FIG. 27, the insect screen 60 is depicted with a broken line, and the circuit board 63 is omitted.

The light-projecting unit 70 is disposed in the outer periphery of the smoke detection chamber 61. The light-receiving unit 80 is disposed at an outer peripheral position that is not directly struck by light from the light-projecting unit 70. In the light-projecting unit 70, a light-projecting element (LED) 71, as a light-emitting section, is housed in a projection cover 72, on the circuit board 63. In the light-receiving unit 80, a light-receiving element (photodiode) 81, as a light-receiving section, is housed in a light-receiving cover 82, on the circuit board 63. The projection cover 72 and the light-receiving cover 82 are formed integrally, together with labyrinth walls 90, a light-blocking wall 100 and so forth described below, on an optical base 110.

The light-transmitting cover 72 has a projection window 73 opened towards the interior of the smoke detection chamber 61. The light-receiving cover 82 has a light-receiving window 83 opened towards the interior of the smoke detection chamber 61. The optical axis of light exiting the projection window 73 and the optical axis of light incident onto the light-receiving window 83 are both substantially parallel to the inner bottom face of the optical base 110.

The light-projecting unit 70 is configured to project light onto a projection area (region enclosed by solid lines 201, 201) defined by the projection window 73 and the light-blocking wall 100, in such a manner that light from the light-projecting element 71 passes through substantially the centers of the projection window 73 and of the smoke detection chamber 61 and arrives to labyrinth walls 91 on the opposite side. The light-receiving unit 80 is configured to receive light from a light reception area (region enclosed by solid lines 202, 202) defined by the light-receiving window 83 and the light-blocking wall 100.

The projection area and the light reception area overlap at substantially the center of the smoke detection chamber 61. A smoke sensing region 203 is formed in the overlapping portion. That is, the smoke detection chamber 61 is configured so that, when light from the light-projecting unit 70 is irradiated onto smoke flowing into the smoke sensing region 203, the light-receiving unit 80 receives light scattered by the smoke and sends a resulting light reception signal to a circuit block, to discriminate thereby the occurrence of fire.

The light-blocking wall 100 is provided so as to shield the light-receiving unit 80 from direct light from the light-projecting unit 70, and is formed in a substantially central position of the region of a short arc 204 formed by the light-projecting unit 70 and the light-receiving unit 80, in such a way so as protrude inwards into the smoke detection chamber 61, from the outer periphery of the latter.

The plurality of labyrinth walls 90 is formed substantially as flat plates that are standingly provided from the inner bottom face of the optical base 110 across the entire height direction (vertical direction) of the smoke detection chamber 61. The labyrinth walls 90 form smoke inflow openings 120, at the end of the outer peripheral side of the labyrinth walls 90 (hereafter referred to as outer end; the end on the opposite side being referred to as inner end), in the respective gaps between two labyrinth walls 90. The labyrinth walls 90 form also smoke inflow channels 121, further inward than the smoke inflow openings 120, in the form of respective gaps surrounded by two labyrinth walls 90.

The labyrinth walls 90 have also the function of blocking ambient light, so as to prevent the smoke detection function from being destabilized due to ambient light that strikes into the smoke detection chamber 61. The labyrinth walls 90 are divided into light projection-side labyrinth walls 91, in the region on the side of the light-receiving unit, and light reception-side labyrinth walls 92, in the region of the side of the light-projecting unit, upon division of the interior of the smoke detection chamber 61 by a centerline L1 that joins the centers of the short arc 204 and of the smoke detection chamber 61. The light projection-side labyrinth walls 91 receive direct light from the light-projecting unit 70, while the light reception-side labyrinth walls 92 prevent ambient light from striking the light-receiving unit 80.

The light projection-side labyrinth walls 91 and the light reception-side labyrinth walls 92 have inner ends 910, 920 that do not face the center of the smoke detection chamber 61, but which face each other across respective inner ends 910, 920. That is, the inner ends 910 of the light projection-side labyrinth walls 91 are oriented counterclockwise, while the inner ends 920 of the light reception-side labyrinth walls 92 are oriented clockwise. As a result, the light projection-side labyrinth walls 91 and the light reception-side labyrinth walls 92 allow smoke to flow in while blocking ambient light, which intrudes via the smoke inflow openings 120, at outward-looking wall faces 913, 923 of the labyrinth walls 91, 92. The light projection-side labyrinth walls 91 are formed to dimensions such that the inner ends 910 thereof do not intrude into the light reception area.

In such a structure, the inward-looking wall faces 912 of the light projection-side labyrinth walls 91 receive direct light coming from the light-projecting unit 70 and that crosses the smoke sensing region 203. Light irradiated onto the inward-looking wall faces 912 is reflected further outward than the light-receiving unit 80, strikes the outward-looking wall faces 913 of adjacent labyrinth walls 91, and exits the smoke detection chamber 61, via the smoke inflow channels 121, in a direction opposite to that of the smoke. Therefore, direct light from the light-projecting unit 70 is not reflected towards the light reception area, even if reflected by the light projection-side labyrinth walls 91 when the light crosses the smoke sensing region 203. Also, the direct light exits to the exterior with an attenuated light intensity. In FIG. 27, the trajectory of light that strikes the light projection-side labyrinth walls 91 and exits to the exterior is indicated by solid lines 205.

By contrast, the inward-looking wall faces 922 of the light reception-side labyrinth walls 92 face towards the side of the light-projecting unit 70. Therefore, in a hypothetical case where light is irradiated from the light-receiving unit 80 towards light reception-side labyrinth walls 92, that light would be led out of the smoke detection chamber 61, through reflection on adjacent labyrinth walls 92, in a manner similar to that of the light projection-side labyrinth walls 91. That is, external light can be prevented from being received by the direct light-receiving unit 80 by arranging the light reception-side labyrinth walls 92 in the above-described way. In FIG. 27, the trajectory of hypothetical light that strikes the light reception-side labyrinth walls 92 is indicated by solid lines 206.

The inward-looking wall faces 922 of the light reception-side labyrinth walls 92 face towards the light-projecting unit 70. Therefore, even when light scattered at, for instance, the inner ends 910 of the light projection-side labyrinth walls 91 is irradiated onto the light reception-side labyrinth walls 92, the resulting reflected light is led out of the smoke detection chamber 61. In FIG. 27, the trajectory of light that is scattered upon striking the light projection-side labyrinth walls 91 is indicated by solid lines 207.

Thus, unwanted light projected from the light-projecting unit 70 and external light can both be prevented from becoming stray light that is directed at the light reception area and/or the light-receiving unit 80, inside the smoke detection chamber 61, by arranging the light projection-side and light reception-side labyrinth walls 91, 92 in the above-described manner. The above configuration enables appropriate smoke inflow, while affording appropriate light shielding. A smoke detection chamber 61 can be configured as a result in which little stray light finds its way.

In a small smoke sensor A as in the present embodiment, in particular, it is difficult to form complex-shaped labyrinth walls, shaped as chevrons or the like, in the smoke detection chamber 61. It is likewise difficult to cause the light intensity of unwanted light to be attenuated through light reflection, on account of the small dimensions of the interior of the smoke detection chamber 61. Therefore, in general, although stray light is likely to occur in arrays of flat plate-like labyrinth walls, the occurrence of stray light can be reduced by employing the above-described configuration.

The configuration is not limited to the above-described one, and the inner ends 910 of the light projection-side labyrinth walls 91 may be oriented clockwise, so that the light projection-side and light reception-side labyrinth walls 91, 92 are both oriented clockwise.

Figure 28:
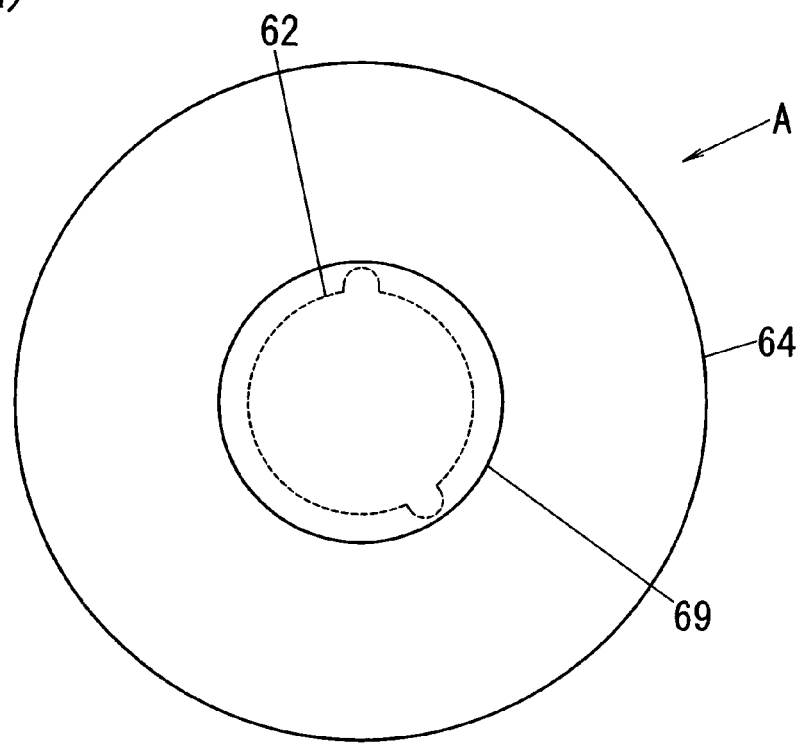
Figure 28:
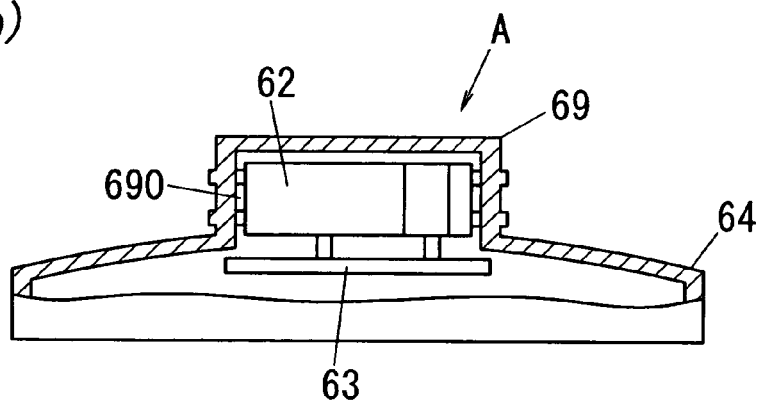

The internal configuration of the above-described smoke detection chamber 61 can also be used in a smoke sensor A in which the smoke detection chamber 61 is disposed so as to protrude in front of the body 64 (so as to protrude downwards, if the smoke sensor 61 is affixed to the ceiling), as illustrated in FIGS. 28(*a*) and 28(*b*). In this smoke sensor A, the smoke detection body 62, comprising the smoke detection chamber 61 and the insect screen 60, is protrudingly disposed in the center of a disc-like body 64. The smoke detection body 62 is protected by being covered with a protector 69. The protector 69 has multiple openings 690 in the outer periphery thereof, such that smoke can flow into the smoke detection chamber 61 via the openings 690.

Embodiment 10

The smoke sensor of the present embodiment has an internal structure of the smoke detection chamber that is different from that of the smoke sensor explained in Embodiment 9.

In Embodiment 9, specifically, the light-blocking wall 100 is a structure wherein a light-blocking body 101 is extendingly provided on a partition wall 102 that in turn extends inwardly from the outer periphery of the smoke detection chamber 61, in such a manner so as to allow partitioning the smoke. The light-blocking body 101 of the present embodiment, by contrast, is structured so as to be standingly provided on its own, in the smoke detection chamber 61, without extending from the partition wall.

Figure 29:
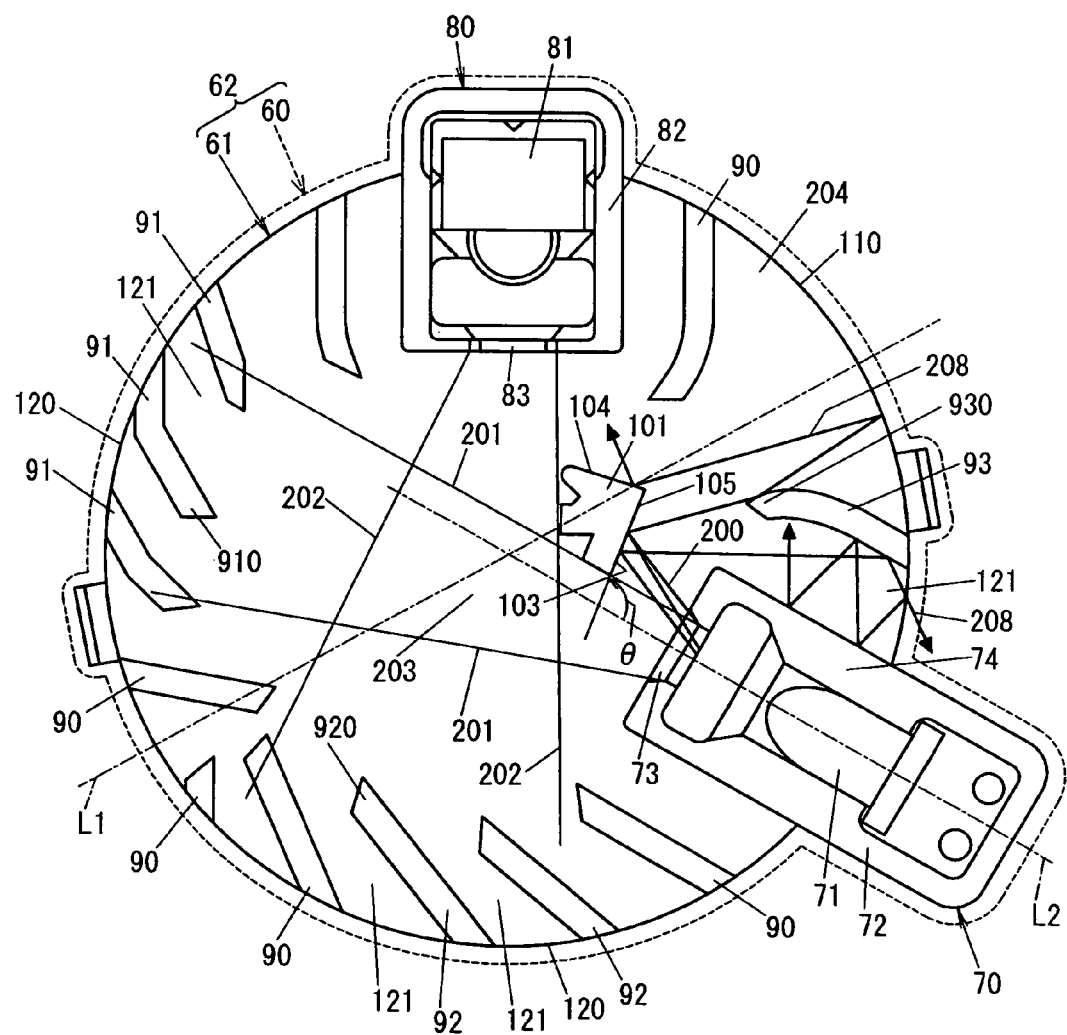
FIG. 29 is a schematic plan-view diagram illustrating the internal structure of a smoke detection chamber in Embodiment 10 of the present invention.

The light-blocking body 101 stands between the projection window 73 and the light-receiving window 83, and limits mainly the light reception area and the projection area, as illustrated in FIG. 29. The projection area is restricted to a region delimited by solid lines 200, 201, in such a manner that the projection area spreads, by a predefined angle, about the center of the projection axis L2, from the width of the opening of the projection window 73. Herein, however, the light-blocking body 101 blocks direct light, as a result of which the projection area is narrowed to within the area of the solid lines 201, 201. The light reception area is likewise narrowed by the light-blocking body 101.

The light-blocking body 101 has also the function of further reflecting, and attenuating the intensity of, direct light from the light-projecting unit 70 and returning light reflected at the smoke detection chamber 61. To that end, various reflecting surfaces are formed on the light-blocking body 101.

In particular, a light-blocking surface 103 that opposes the projection window 73 is a surface that reflects direct light from the light-projecting unit 70. As illustrated in FIG. 29, the light-blocking surface 103 is formed slightly opened outwards, aiming a front face of the projection window 73. In other words, the light-blocking surface 103 forms an obtuse angle with the projection axis L2 of the light-projecting unit 70. As a result, direct light that strikes the light-blocking surface 103 is reflected towards a region of a short arc 110. In FIG. 29, the reference numeral 208 denotes the trajectory of light that strikes the light-blocking surface 103.

The angle θ formed between the light-blocking surface 103 and the projection axis L2 faces a smoke inflow channel 121 formed by a side wall 74 of the projection cover 72 and a labyrinth wall 93 on the side of the short arc 110, as in the example illustrated in FIG. 29. Reflected light is gathered in the narrow region flanked by the light-projecting unit 70 and the light-receiving unit 80, as a result of which light becomes reflected repeatedly within this narrow space. The intensity of the light can be attenuated thereby. Light repeatedly reflected within the smoke inflow channel 121 exits ultimately the smoke detection chamber 61, or is rendered very weak, if detained in the smoke detection chamber 61. Stray light derived from light being reflected on the light-blocking body 101 can be reduced as a result.

An effect similar to that of the present embodiment can be expected to be achieved by using the same configuration (light-blocking surface 103) of the light-blocking body 101 as in the present embodiment also in a case where there is used a light-blocking wall 100 where the light-blocking body 101 is extendingly provided on the partition wall 102, as in Embodiment 9.

In the example of FIG. 29, the figure shows the trajectory of light that is reflected on the light-blocking surface 103, strikes an inner end 930 of a labyrinth wall 93, and returns to another reflecting surface 104 of the light-blocking body 101. In the example of the figure, this returning reflected light is directed at the front face of the light-receiving unit 80. However, that light as well is reflected at various sites, as a result of which the light intensity thereof is weakened enough so as to pose virtually no problem to normal light reception by the light-receiving unit 80. In terms of a balance with smoke inflow, the reflecting surface 104 stands preferably at an angle such that the light reflected thereon is led out of the smoke detection chamber 61.

The light-blocking surface 103 has also an auxiliary surface 105 that extends outside the projection area defined by the projection window 73. Therefore, direct light can be blocked, without leaks, while reflected incoming light is then further reflected at the auxiliary surface 105. Light intensity can be attenuated thereby.

Other features and functions are identical to those of Embodiment 9.

The features explained in the various embodiments above can be used in appropriate combinations.

The invention claimed is:

1. A smoke sensor, comprising:
a light-emitting section;
a light-receiving section;
a current-voltage conversion circuit;
a current source; and
a determination processing section,
wherein the light-emitting section outputs pulsed light towards a sensing space at a predefined sensing period,
the light-receiving section is disposed at a position not struck by direct light from the light-emitting section, but struck by light from the light-emitting section, that is diffused and reflected by smoke that flows into the sensing space,
the current source causes a sensor current of a magnitude corresponding to a light reception intensity to flow in the light-receiving section,
the current-voltage conversion circuit has a conversion section, the conversion section converts an input current to an output voltage and outputs the output voltage from an output terminal, and the input current is inputted into an input terminal of the conversion section connected to the light-receiving section,
the determination processing section determines presence or absence of the smoke in the sensing space on a basis of the output voltage,
the current-voltage conversion circuit has low-frequency correction means, and
the low-frequency correction means extracts, of the output voltage, a low-frequency component that is not greater than or equal to a cut-off frequency that is lower than a frequency of a pulsed detection signal that is generated when the light-receiving section receives light from the light-emitting section, causes a flow of a correction current of a magnitude according to the low-frequency component, and uses a combined current of the correction current and the input current as the sensor current, to reduce thereby the input current by the correction current.

2. The smoke sensor according to claim 1, wherein the sensor current is a current flowing from the light-receiving section into the input terminal, and
the low-frequency correction means extracts, from the light-receiving section, a current of a magnitude corresponding to the correction current.

3. The smoke sensor according to claim 1, wherein the sensor current is a current flowing from the conversion section into the light-receiving section, and
the low-frequency correction means supplies, to the light-receiving section, a current of a magnitude corresponding to the correction current.

4. The smoke sensor according to claim 2, wherein the low-frequency correction means comprises a first feedback circuit and a correcting transistor,
the first feedback circuit outputs, of the output voltage, a low-frequency component that is not greater than or equal to a first cut-off frequency that is lower than a frequency of the detection signal, and
the correcting transistor is inserted between a predefined potential point and the input terminal, and a control terminal is connected to an output of the first feedback circuit, whereby the correction current of a magnitude according to the output of the first feedback circuit is caused to flow.

5. The smoke sensor according to claim 4, wherein the low-frequency correction means comprises a second feedback circuit and a correcting resistor,
the second feedback circuit outputs, of the output voltage, a voltage corresponding to a low-frequency component that is not greater than or equal to a second cut-off frequency that is lower than a frequency of the detection signal, and
the correcting resistor is inserted between an output of the second feedback circuit and the input terminal, and causes a flow of the correction current of a magnitude according to the output of the second feedback circuit.

6. The smoke sensor according to claim 3, wherein the low-frequency correction means comprises a first feedback circuit and a correcting transistor,
the first feedback circuit outputs, of the output voltage, a low-frequency component that is not greater than or equal to a first cut-off frequency that is lower than a frequency of the detection signal, and
the correcting transistor is inserted between a predefined potential point and the input terminal, and a control terminal is connected to an output of the first feedback circuit, whereby the correction current of a magnitude according to the output of the first feedback circuit is caused to flow.

7. The smoke sensor according to claim 6, wherein the low-frequency correction means comprises a second feedback circuit and a correcting resistor,
the second feedback circuit outputs, of the output voltage, a voltage corresponding to a low-frequency component that is not greater than or equal to a second cut-off frequency that is lower than a frequency of the detection signal, and
the correcting resistor is inserted between an output of the second feedback circuit and the input terminal, and causes the flow of the correction current of a magnitude according to the output of the second feedback circuit.

8. The smoke sensor according to claim 5, wherein the first feedback circuit has frequency switching means, and
the frequency switching means switches the first cut-off frequency to be lower than the second cut-off frequency at the sensing period, and higher than the second cut-off frequency, at a period other than the sensing period.

9. The smoke sensor according to claim 8, wherein the first feedback circuit has an integrating circuit that outputs an integration value component of the output voltage,
the frequency switching means comprises a sample-and-hold-circuit, the sample-and-hold-circuit has a first switch inserted between an output of the integrating circuit and the control terminal of the correcting transistor, and
at the sensing period, the frequency switching means switches off the first switch, to operate thereby the sample-and-hold-circuit, and applies a held output voltage of the integrating circuit to the control terminal of the correcting transistor.

10. The smoke sensor according to claim 9, wherein a second switch is connected between the output terminal and the input terminal of the conversion section, and
the second switch is switched on when the first switch is on.

11. The smoke sensor according to claim 9, wherein an off-resistance value of the first switch is set to be smaller than a resistance value between the predefined potential point and the control terminal of the correcting transistor.

12. The smoke sensor according to claim 8, wherein the first feedback circuit has an integrating circuit that outputs an integration value component of the output voltage,
the frequency switching means comprises a low-pass filter circuit, the low-pass filter circuit has a parallel circuit of a capacitor, a resistor and a third switch,
the capacitor is connected between the predefined potential point and the control terminal of the correcting transistor,
the parallel circuit is connected between the control terminal of the correcting transistor and an output of the integrating circuit, and
at the sensing period, the frequency switching means switches off the third switch, to operate thereby the low-pass filter circuit.

13. The smoke sensor according to claim 8, wherein the first feedback circuit has an integrating circuit, the integrating circuit has a time constant determined by a first resistor and a capacitor,
the frequency switching means comprises a series circuit of a second resistor and a fourth switch, the series circuit is connected in parallel to the first resistor, and
at the sensing period, the frequency switching means switches off the fourth switch.

14. The smoke sensor according to claim 5, wherein the second feedback circuit comprises a second active filter, the second active filter outputs a voltage of opposite phase to the input current, and
the first feedback circuit comprises a first active filter, the first active filter outputs a voltage in-phase with the input current.

15. The smoke sensor according to claim 7, wherein the second feedback circuit comprises a second active filter, the second active filter outputs a voltage in-phase with a current that is supplied from the conversion section to the light-receiving section, and
the first feedback circuit comprises a first active filter, the first active filter outputs a voltage of opposite phase to a current that is supplied from the conversion section to the light-receiving section.

16. The smoke sensor according to claim 4, wherein the correcting transistor is provided in a plurality,
the current-voltage conversion circuit comprises selection switches and a switch control circuit,
the selection switches are inserted between the input terminal and the respective correcting transistors, and
the switch control circuit controls switching-on and -off of the selection switches in accordance with the output of the first feedback circuit in such a manner that the number of the selection switches that are switched on is greater as the output of the first feedback circuit is greater.

17. The smoke sensor according to claim 14, wherein the first feedback circuit and the second feedback circuit share an operational amplifier,
the current-voltage conversion circuit comprises mode switching means, the mode switching means switches between an operation mode of using the operational amplifier in the first feedback circuit, and an operation mode of using the operational amplifier in the second feedback circuit.

18. The smoke sensor according to claim 14, wherein a power source voltage of the first feedback circuit is set to be higher than the power source voltage of other circuits.

* * * * *